US012653955B2

(12) United States Patent
Barchen et al.

(10) Patent No.: US 12,653,955 B2
(45) Date of Patent: Jun. 16, 2026

(54) ANTI-ROTATION CARTRIDGE PIN

(71) Applicant: West Pharma. Services IL, Ltd., Ra'anana (IL)

(72) Inventors: Lior Barchen, Gani Tal (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 1054 days.

(21) Appl. No.: 17/734,093

(22) Filed: May 1, 2022

(65) Prior Publication Data

US 2022/0249777 A1 Aug. 11, 2022

Related U.S. Application Data

(62) Division of application No. 16/321,697, filed as application No. PCT/US2016/068065 on Dec. 21, 2016, now Pat. No. 11,338,090.

(60) Provisional application No. 62/369,492, filed on Aug. 1, 2016.

(51) Int. Cl.
  A61M 5/28 (2006.01)
  A61M 5/145 (2006.01)
  A61M 5/24 (2006.01)

(52) U.S. Cl.
  CPC .......... A61M 5/283 (2013.01); A61M 5/1456 (2013.01); A61M 2005/14573 (2013.01); A61M 2005/2477 (2013.01); A61M 2205/582 (2013.01)

(58) Field of Classification Search
  CPC ...... A61M 2005/14573; A61M 5/1456; A61M 2005/2477; A61M 5/283; A61M 2205/582; A61M 2005/2407; A61M 5/28; A61M 5/24; A61M 2005/2437; A61M 2005/2481; A61J 1/062
  See application file for complete search history.

(56) References Cited

U.S. PATENT DOCUMENTS

| | | | |
|---|---|---|---|
| 232,432 | A | 9/1880 | Allison |
| 1,125,887 | A | 1/1915 | Schimmel |
| 1,321,550 | A | 11/1919 | Frank et al. |

(Continued)

FOREIGN PATENT DOCUMENTS

| | | |
|---|---|---|
| CN | 1505535 A | 6/2004 |
| CN | 1747683 A | 3/2006 |

(Continued)

OTHER PUBLICATIONS

US 8,333,733 B2, 12/2012, Lanigan et al. (withdrawn)

(Continued)

*Primary Examiner* — Theodore J Stigell
*Assistant Examiner* — Benjamin Koo
(74) *Attorney, Agent, or Firm* — Blank Rome LLP

(57) ABSTRACT

A system for inserting a pharmaceutical cartridge into a delivery device is described. The cartridge can be inserted in an arbitrary orientation and the system reorients the cartridge to a locked orientation. For example, a driver applies a torque to the cartridge to cause the reorienting. The torque rotates the cartridge around an axis thereof until the cartridge reaches the locked orientation. When the cartridge reaches the locked orientation, an interference element on the cartridge interlocks with a complementary interference element on the delivery device to lock the cartridge in the locked orientation. Once the cartridge is locked in the second orientation, the torque causes discharge the pharmaceutical.

17 Claims, 13 Drawing Sheets

(56) References Cited

U.S. PATENT DOCUMENTS

| | | |
|---|---|---|
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A | 12/1987 | Henri et al. |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A | 9/1994 | Sweeney et al. |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Oesterlind et al. |
| 5,690,618 A | 11/1997 | Smith et al. |
| 5,697,908 A | 12/1997 | Imbert et al. |
| 5,697,916 A | 12/1997 | Schraga |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |

(56)                 References Cited

U.S. PATENT DOCUMENTS

| | | | |
|---|---|---|---|
| 5,926,596 | A | 7/1999 | Edwards et al. |
| 5,931,814 | A | 8/1999 | Alex et al. |
| 5,941,850 | A | 8/1999 | Shah et al. |
| 5,944,699 | A | 8/1999 | Barrelle et al. |
| 5,948,392 | A | 9/1999 | Haslwanter et al. |
| 5,954,697 | A | 9/1999 | Srisathapat et al. |
| 5,957,895 | A | 9/1999 | Sage et al. |
| 5,968,011 | A | 10/1999 | Arsen et al. |
| 5,989,221 | A | 11/1999 | Hjertman |
| 5,993,423 | A | 11/1999 | Choi |
| 6,004,296 | A | 12/1999 | Jansen et al. |
| 6,004,297 | A | 12/1999 | Steenfeldt-Jensen et al. |
| 6,033,245 | A | 3/2000 | Yamkovoy |
| 6,033,377 | A | 3/2000 | Rasmussen et al. |
| 6,045,533 | A | 4/2000 | Kriesel et al. |
| 6,064,797 | A | 5/2000 | Crittendon et al. |
| 6,074,369 | A | 6/2000 | Sage et al. |
| 6,162,197 | A | 12/2000 | Mohammad |
| 6,186,979 | B1 | 2/2001 | Dysarz |
| 6,186,982 | B1 | 2/2001 | Gross et al. |
| 6,189,292 | B1 | 2/2001 | Odell et al. |
| 6,200,289 | B1 | 3/2001 | Hochman et al. |
| 6,200,296 | B1 | 3/2001 | Dibiasi et al. |
| 6,224,569 | B1 | 5/2001 | Brimhall |
| 6,248,093 | B1 | 6/2001 | Moberg |
| 6,270,481 | B1 | 8/2001 | Mason et al. |
| 6,277,095 | B1 | 8/2001 | Kriesel et al. |
| 6,277,098 | B1 | 8/2001 | Klitmose et al. |
| 6,277,099 | B1 | 8/2001 | Strowe et al. |
| 6,287,283 | B1 | 9/2001 | Ljunggreen et al. |
| 6,293,925 | B1 | 9/2001 | Safabash et al. |
| 6,302,633 | B1 | 10/2001 | Poe |
| 6,336,729 | B1 | 1/2002 | Pavelle et al. |
| 6,345,968 | B1 | 2/2002 | Shupe |
| 6,362,591 | B1 | 3/2002 | Moberg |
| 6,377,848 | B1 | 4/2002 | Garde et al. |
| 6,391,005 | B1 | 5/2002 | Lum et al. |
| 6,423,029 | B1 | 7/2002 | Elsberry |
| D461,243 | S | 8/2002 | Niedospial |
| D465,026 | S | 10/2002 | May et al. |
| 6,458,102 | B1 | 10/2002 | Mann et al. |
| 6,485,461 | B1 | 11/2002 | Mason et al. |
| 6,485,465 | B2 | 11/2002 | Moberg et al. |
| 6,500,150 | B1 | 12/2002 | Gross et al. |
| 6,503,231 | B1 | 1/2003 | Prausnitz et al. |
| 6,511,336 | B1 | 1/2003 | Turek et al. |
| 6,517,517 | B1 | 2/2003 | Farrugia et al. |
| D471,274 | S | 3/2003 | Diaz et al. |
| D471,983 | S | 3/2003 | Hippolyte et al. |
| 6,554,800 | B1 | 4/2003 | Nezhadian et al. |
| 6,555,986 | B2 | 4/2003 | Moberg |
| 6,558,351 | B1 | 5/2003 | Steil et al. |
| 6,565,541 | B2 | 5/2003 | Sharp |
| 6,585,695 | B1 | 7/2003 | Adair et al. |
| 6,589,229 | B1 | 7/2003 | Connelly et al. |
| 6,595,956 | B1 | 7/2003 | Gross et al. |
| 6,595,960 | B2 | 7/2003 | West et al. |
| 6,645,181 | B1 | 11/2003 | Lavi et al. |
| 6,652,482 | B2 | 11/2003 | Hochman |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,673,033 | B1 | 1/2004 | Sciulli et al. |
| 6,679,862 | B2 | 1/2004 | Diaz et al. |
| 6,685,678 | B2 | 2/2004 | Evans et al. |
| 6,689,118 | B2 | 2/2004 | Alchas et al. |
| 6,699,218 | B2 | 3/2004 | Flaherty et al. |
| 6,719,141 | B2 | 4/2004 | Heinz et al. |
| 6,722,916 | B2 | 4/2004 | Buccinna et al. |
| 6,743,211 | B1 | 6/2004 | Prausnitz et al. |
| 6,749,587 | B2 | 6/2004 | Flaherty |
| 6,752,783 | B2 | 6/2004 | Hung et al. |
| 6,752,787 | B1 | 6/2004 | Causey et al. |
| 6,767,336 | B1 | 7/2004 | Kaplan |
| 6,768,425 | B2 | 7/2004 | Flaherty et al. |
| 6,786,890 | B2 | 9/2004 | Preuthun et al. |
| 6,800,071 | B1 | 10/2004 | Mcconnell et al. |
| 6,805,687 | B2 | 10/2004 | Dextradeur et al. |
| 6,817,990 | B2 | 11/2004 | Yap et al. |
| 6,824,529 | B2 | 11/2004 | Gross et al. |
| 6,843,782 | B2 | 1/2005 | Gross et al. |
| 6,854,620 | B2 | 2/2005 | Ramey |
| 6,905,298 | B1 | 6/2005 | Haring |
| 6,907,679 | B2 | 6/2005 | Yarborough et al. |
| 6,908,452 | B2 | 6/2005 | Diaz et al. |
| 6,960,192 | B1 | 11/2005 | Flaherty et al. |
| 6,979,316 | B1 | 12/2005 | Rubin et al. |
| 6,997,727 | B1 | 2/2006 | Legrady et al. |
| 7,001,360 | B2 | 2/2006 | Veasey et al. |
| 7,004,104 | B1 | 2/2006 | Kundus |
| 7,004,929 | B2 | 2/2006 | McWethy et al. |
| 7,025,226 | B2 | 4/2006 | Ramey |
| 7,033,338 | B2 | 4/2006 | Vilks et al. |
| 7,034,223 | B2 | 4/2006 | Fan et al. |
| 7,048,715 | B2 | 5/2006 | Diaz et al. |
| 7,060,054 | B2 | 6/2006 | Nissels |
| 7,060,059 | B2 | 6/2006 | Keith et al. |
| 7,063,684 | B2 | 6/2006 | Moberg |
| 7,066,909 | B1 | 6/2006 | Peter et al. |
| 7,094,221 | B2 | 8/2006 | Veasey et al. |
| 7,097,637 | B2 | 8/2006 | Triplett et al. |
| 7,112,187 | B2 | 9/2006 | Karlsson |
| 7,128,727 | B2 | 10/2006 | Flaherty et al. |
| 7,144,384 | B2 | 12/2006 | Gorman et al. |
| 7,193,521 | B2 | 3/2007 | Moberg et al. |
| D544,092 | S | 6/2007 | Lewis |
| 7,225,694 | B2 | 6/2007 | Said |
| 7,247,149 | B2 | 7/2007 | Beyerlein |
| 7,250,037 | B2 | 7/2007 | Shermer et al. |
| 7,267,669 | B2 | 9/2007 | Staunton et al. |
| RE39,923 | E | 11/2007 | Blom |
| 7,291,132 | B2 | 11/2007 | Deruntz et al. |
| 7,291,159 | B2 | 11/2007 | Schmelzeisen-Redeker et al. |
| 7,303,549 | B2 | 12/2007 | Flaherty et al. |
| 7,306,578 | B2 | 12/2007 | Gray et al. |
| 7,326,194 | B2 | 2/2008 | Zinger et al. |
| 7,344,385 | B2 | 3/2008 | Chen |
| 7,364,570 | B2 | 4/2008 | Gerondale et al. |
| 7,377,912 | B2 | 5/2008 | Graf et al. |
| 7,390,312 | B2 | 6/2008 | Barrelle |
| 7,390,314 | B2 | 6/2008 | Stutz et al. |
| 7,407,493 | B2 | 8/2008 | Cane |
| 7,418,880 | B1 | 9/2008 | Smith |
| D578,210 | S | 10/2008 | Muta et al. |
| 7,442,186 | B2 | 10/2008 | Blomquist |
| 7,455,663 | B2 | 11/2008 | Bikovsky |
| 7,465,290 | B2 | 12/2008 | Reilly |
| 7,468,055 | B2 | 12/2008 | Prais et al. |
| 7,488,181 | B2 | 2/2009 | Van |
| 7,497,842 | B2 | 3/2009 | Diaz et al. |
| 7,500,963 | B2 | 3/2009 | Westbye et al. |
| 7,501,587 | B2 | 3/2009 | English |
| 7,503,786 | B2 | 3/2009 | Kato et al. |
| 7,530,964 | B2 | 5/2009 | Avi et al. |
| 7,540,858 | B2 | 6/2009 | Dibiasi |
| 7,547,281 | B2 | 6/2009 | Hayes et al. |
| 7,565,208 | B2 | 7/2009 | Harris et al. |
| 7,569,050 | B2 | 8/2009 | Moberg et al. |
| D600,341 | S | 9/2009 | Loerwald |
| 7,585,287 | B2 | 9/2009 | Bresina et al. |
| 7,588,559 | B2 | 9/2009 | Aravena et al. |
| 7,589,974 | B2 | 9/2009 | Grady et al. |
| D602,155 | S | 10/2009 | Foley et al. |
| D602,586 | S | 10/2009 | Foley et al. |
| 7,597,682 | B2 | 10/2009 | Moberg |
| D604,835 | S | 11/2009 | Conley |
| 7,611,491 | B2 | 11/2009 | Pickhard |
| 7,621,893 | B2 | 11/2009 | Moberg et al. |
| 7,628,770 | B2 | 12/2009 | Ethelfeld |
| 7,628,772 | B2 | 12/2009 | Mcconnell et al. |
| 7,628,782 | B2 | 12/2009 | Adair et al. |
| 7,637,891 | B2 | 12/2009 | Wall |
| 7,637,899 | B2 | 12/2009 | Woolston et al. |
| 7,641,649 | B2 | 1/2010 | Moberg et al. |

(56)                    References Cited

U.S. PATENT DOCUMENTS

| | | | |
|---|---|---|---|
| 7,658,734 B2 | 2/2010 | Adair et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,766,873 B2 | 8/2010 | Moberg et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Wang et al. |
| 7,857,131 B2 | 12/2010 | Vedrine |
| 7,879,025 B2 | 2/2011 | Jacobson et al. |
| 7,892,206 B2 | 2/2011 | Moberg et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 7,998,131 B2 | 8/2011 | Adair et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,034,026 B2 | 10/2011 | Grant et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Stoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,447 B2 | 5/2012 | Moberg et al. |
| 8,182,462 B2 | 5/2012 | Stoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,257,345 B2 | 9/2012 | Adair et al. |
| 8,267,893 B2 | 9/2012 | Moberg et al. |
| 8,267,921 B2 | 9/2012 | Yodfat et al. |
| 8,273,061 B2 | 9/2012 | Mcconnell et al. |
| 8,287,520 B2 | 10/2012 | Drew et al. |
| 8,292,647 B1 | 10/2012 | Mcgrath et al. |
| 8,303,572 B2 | 11/2012 | Adair et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Indegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,500,716 B2 | 8/2013 | Adair et al. |
| 8,512,287 B2 | 8/2013 | Cindrich et al. |
| 8,512,295 B2 | 8/2013 | Evans et al. |
| 8,517,987 B2 | 8/2013 | Stoc et al. |
| 8,517,992 B2 | 8/2013 | Jones |
| 8,523,803 B1 | 9/2013 | Favreau |
| 8,551,046 B2 | 10/2013 | Causey et al. |
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,617,110 B2 | 12/2013 | Moberg et al. |
| 8,622,966 B2 | 1/2014 | Causey et al. |
| 8,628,510 B2 | 1/2014 | Bazargan et al. |
| 8,632,499 B2 | 1/2014 | Grant et al. |
| 8,647,074 B2 | 2/2014 | Moberg et al. |
| 8,647,296 B2 | 2/2014 | Moberg et al. |
| 8,647,303 B2 | 2/2014 | Cowe |
| 8,668,672 B2 | 3/2014 | Moberg et al. |
| 8,674,288 B2 | 3/2014 | Hanson et al. |

(56) References Cited

U.S. PATENT DOCUMENTS

| | | | |
|---|---|---|---|
| 8,679,060 B2 | 3/2014 | Mernoe et al. |
| 8,681,010 B2 | 3/2014 | Moberg et al. |
| D702,834 S | 4/2014 | Norton et al. |
| 8,690,855 B2 | 4/2014 | Alderete et al. |
| 8,708,961 B2 | 4/2014 | Field et al. |
| 8,715,237 B2 | 5/2014 | Moberg et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Weinandy |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,845,587 B2 | 9/2014 | Lanigan et al. |
| 8,858,508 B2 | 10/2014 | Lavi et al. |
| 8,864,739 B2 | 10/2014 | Moberg et al. |
| 8,876,770 B2 | 11/2014 | Kraft et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,371 B2 | 4/2015 | Moberg et al. |
| 9,011,387 B2 | 4/2015 | Ekman et al. |
| 9,033,925 B2 | 5/2015 | Moberg et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,107,999 B2 | 8/2015 | Moberg et al. |
| 9,138,534 B2 | 9/2015 | Yodfat et al. |
| 9,149,575 B2 | 10/2015 | Cabiri |
| 9,173,996 B2 | 11/2015 | Gray et al. |
| 9,173,997 B2 | 11/2015 | Gross et al. |
| 9,180,248 B2 | 11/2015 | Moberg et al. |
| 9,205,188 B2 | 12/2015 | Lanigan et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,318 B2 | 4/2016 | Lanigan et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,339,607 B2 | 5/2016 | Langley et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,364,608 B2 | 6/2016 | Moberg et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,433,732 B2 | 9/2016 | Moberg et al. |
| 9,433,733 B2 | 9/2016 | Moberg et al. |
| 9,446,188 B2 | 9/2016 | Grant et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,452 B2 | 2/2017 | Adair et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,048 B2 | 2/2019 | Gray et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | Mcloughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,500,352 B2 | 12/2019 | Grant et al. |
| 10,561,798 B2 | 2/2020 | Holland et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,729,847 B2 | 8/2020 | Gray et al. |
| 10,758,679 B2 | 9/2020 | Bar-El et al. |
| 10,842,942 B2 | 11/2020 | Iibuchi et al. |
| 11,027,059 B2 | 6/2021 | Niklaus et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2002/0173748 A1 | 11/2002 | McConnell et al. |

(56)　　　　　　　References Cited

U.S. PATENT DOCUMENTS

| | | | |
|---|---|---|---|
| 2002/0173769 A1 | 11/2002 | Gray et al. |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0130618 A1 | 7/2003 | Gray et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0003493 A1 | 1/2004 | Adair et al. |
| 2004/0010207 A1 | 1/2004 | Flaherty et al. |
| 2004/0049160 A1 | 3/2004 | Hsieh et al. |
| 2004/0049161 A1 | 3/2004 | Shearn |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197626 A1 | 9/2005 | Moberg et al. |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0221523 A1 | 9/2008 | Moberg et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |

(56)            References Cited

U.S. PATENT DOCUMENTS

| | | |
|---|---|---|
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0241103 A1 | 9/2010 | Kraft et al. |
| 2010/0256486 A1 | 10/2010 | Savage |
| 2010/0264931 A1 | 10/2010 | Indegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0310807 A1 | 11/2013 | Adair et al. |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207104 A1 | 7/2014 | Vouillamoz et al. |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2014/0364808 A1 | 12/2014 | Niklaus et al. |
| 2015/0005703 A1 | 1/2015 | Hutchinson et al. |
| 2015/0073344 A1 | 3/2015 | Van Damme et al. |
| 2015/0088071 A1 | 3/2015 | Cabiri |

(56) References Cited

U.S. PATENT DOCUMENTS

| | | |
|---|---|---|
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0220755 A1 | 8/2016 | Lanigan et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0339168 A1 | 11/2016 | Hutchinson et al. |
| 2016/0346478 A1 | 12/2016 | Bar-El et al. |
| 2016/0354553 A1 | 12/2016 | Anderson et al. |
| 2017/0007774 A1 | 1/2017 | Brockmeier |
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0133413 A1 | 5/2018 | Grant et al. |
| 2018/0214637 A1 | 8/2018 | Kemp et al. |
| 2018/0304029 A1 | 10/2018 | Koch et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0099549 A1 | 4/2019 | Lanigan et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0164151 A1 | 5/2020 | Farris et al. |
| 2020/0215270 A1 | 7/2020 | Ogawa et al. |
| 2020/0297929 A1 | 9/2020 | Zhang |
| 2020/0360602 A1 | 11/2020 | Gray et al. |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 102917739 | 2/2013 |
| CN | 102958550 | 3/2013 |
| CN | 104334216 | 2/2015 |
| CN | 104394912 | 3/2015 |
| CN | 105102025 A | 11/2015 |
| CN | 105324140 | 2/2016 |
| DE | 0855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0851774 A1 | 7/1998 |

| | | |
|---|---|---|
| EP | 0925082 A1 | 6/1999 |
| EP | 1003581 A1 | 5/2000 |
| EP | 1003581 B1 | 11/2000 |
| EP | 1124600 A1 | 8/2001 |
| EP | 1219312 A2 | 7/2002 |
| EP | 1372762 A1 | 1/2004 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1904130 A2 | 4/2008 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2819724 A1 | 1/2015 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| EP | 3266478 B1 | 1/2020 |
| FR | 2770136 A1 | 4/1999 |
| GB | 2436526 A | 10/2007 |
| JP | 62-112566 A | 5/1987 |
| JP | 01-172843 U | 12/1989 |
| JP | 05-062828 A | 3/1993 |
| JP | 07-194701 A | 8/1995 |
| JP | 3035448 U | 3/1997 |
| JP | H09505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006-525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009-502273 A | 1/2009 |
| JP | 2009-101093 A | 5/2009 |
| JP | 2010-501281 A | 1/2010 |
| JP | 2010-540054 A | 12/2010 |
| JP | 2010-540156 A | 12/2010 |
| JP | 2011-136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |

(56)　　　　　References Cited

FOREIGN PATENT DOCUMENTS

| JP | 2014-518743 | A | 8/2014 |
| JP | 2014-521443 | A | 8/2014 |
| JP | 2014-525339 | A | 9/2014 |
| JP | 2015-514486 | A | 5/2015 |
| JP | 2016-525428 | A | 8/2016 |
| JP | 2016-530016 | A | 9/2016 |
| WO | 90/09202 | A1 | 8/1990 |
| WO | 93/07922 | A1 | 4/1993 |
| WO | 94/07553 | A1 | 4/1994 |
| WO | 94/15660 | A1 | 7/1994 |
| WO | 95/13838 | A1 | 5/1995 |
| WO | 96/09083 | A1 | 3/1996 |
| WO | 96/32975 | A1 | 10/1996 |
| WO | 97/00091 | A1 | 1/1997 |
| WO | 97/10012 | A1 | 3/1997 |
| WO | 97/21457 | A1 | 6/1997 |
| WO | 97/33638 | A1 | 9/1997 |
| WO | 98/57683 | A1 | 12/1998 |
| WO | 98/57686 | A1 | 12/1998 |
| WO | 99/29151 | A1 | 6/1999 |
| WO | 99/38554 | A1 | 8/1999 |
| WO | 99/59665 | A1 | 11/1999 |
| WO | 00/25844 | A1 | 5/2000 |
| WO | 00/69509 | A1 | 11/2000 |
| WO | 01/30415 | A2 | 5/2001 |
| WO | 01/30421 | A2 | 5/2001 |
| WO | 01/70304 | A1 | 9/2001 |
| WO | 01/72357 | A2 | 10/2001 |
| WO | 01/87384 | A1 | 11/2001 |
| WO | 01/89607 | A2 | 11/2001 |
| WO | 01/89613 | A1 | 11/2001 |
| WO | 02/02165 | A2 | 1/2002 |
| WO | 02/04049 | A1 | 1/2002 |
| WO | 02/34315 | A1 | 5/2002 |
| WO | 02/38204 | A2 | 5/2002 |
| WO | 02/56934 | A2 | 7/2002 |
| WO | 02/56943 | A2 | 7/2002 |
| WO | 02/72182 | A1 | 9/2002 |
| WO | 03/62672 | A1 | 7/2003 |
| WO | 03/90833 | A1 | 11/2003 |
| WO | 2004/000397 | A1 | 12/2003 |
| WO | 2004/032990 | A2 | 4/2004 |
| WO | 2004/098684 | A2 | 11/2004 |
| WO | 2004/105841 | A1 | 12/2004 |
| WO | 2005/018703 | A2 | 3/2005 |
| WO | 2005/037350 | A2 | 4/2005 |
| WO | 2005/070485 | A1 | 8/2005 |
| WO | 2005/072795 | A2 | 8/2005 |
| WO | 2006/018617 | A1 | 2/2006 |
| WO | 2006/037434 | A1 | 4/2006 |
| WO | 2006/052737 | A1 | 5/2006 |
| WO | 2006/069380 | A1 | 6/2006 |
| WO | 2006/102676 | A1 | 9/2006 |
| WO | 2006/104806 | A2 | 10/2006 |
| WO | 2006/121921 | A2 | 11/2006 |
| WO | 2007/017052 | A1 | 2/2007 |
| WO | 2007/051563 | A1 | 5/2007 |
| WO | 2007/056504 | A1 | 5/2007 |
| WO | 2007/073228 | A1 | 6/2007 |
| WO | 2007066152 | A2 | 6/2007 |
| WO | 2007/119178 | A2 | 10/2007 |
| WO | 2008/001377 | A2 | 1/2008 |
| WO | 2008/014908 | A1 | 2/2008 |
| WO | 2008/057976 | A2 | 5/2008 |
| WO | 2008/072229 | A2 | 6/2008 |
| WO | 2008/076459 | A1 | 6/2008 |
| WO | 2008/078318 | A2 | 7/2008 |
| WO | 2009/019438 | A1 | 2/2009 |
| WO | 2009/022132 | A2 | 2/2009 |
| WO | 2009/043000 | A1 | 4/2009 |
| WO | 2009/043564 | A1 | 4/2009 |
| WO | 2009/044401 | A2 | 4/2009 |
| WO | 2009/046989 | A2 | 4/2009 |
| WO | 2009/069064 | A1 | 6/2009 |
| WO | 2009/125398 | A2 | 10/2009 |
| WO | 2009/144085 | A2 | 12/2009 |
| WO | 2010/078227 | A1 | 7/2010 |
| WO | 2010/078242 | A1 | 7/2010 |
| WO | 2010/089313 | A1 | 8/2010 |
| WO | 2011/075105 | A1 | 6/2011 |
| WO | 2011/090955 | A1 | 7/2011 |
| WO | 2011/090956 | A2 | 7/2011 |
| WO | 2011/101378 | A1 | 8/2011 |
| WO | 2011/110872 | A1 | 9/2011 |
| WO | 2011/124631 | A1 | 10/2011 |
| WO | 2011/129175 | A1 | 10/2011 |
| WO | 2011/131778 | A1 | 10/2011 |
| WO | 2011/131780 | A2 | 10/2011 |
| WO | 2011/131781 | A1 | 10/2011 |
| WO | 2011/133823 | A1 | 10/2011 |
| WO | 2011/156373 | A1 | 12/2011 |
| WO | 2012/003221 | A1 | 1/2012 |
| WO | 2012/032411 | A2 | 3/2012 |
| WO | 2012/040528 | A1 | 3/2012 |
| WO | 2012/145752 | A2 | 10/2012 |
| WO | 2012/160157 | A1 | 11/2012 |
| WO | 2012/168691 | A1 | 12/2012 |
| WO | 2013/036602 | A1 | 3/2013 |
| WO | 2013/058697 | A1 | 4/2013 |
| WO | 2013/115843 | A1 | 8/2013 |
| WO | 2014/132293 | A1 | 9/2014 |
| WO | 2014/179117 | A1 | 11/2014 |
| WO | 2014/179774 | A1 | 11/2014 |
| WO | 2014/194183 | A2 | 12/2014 |
| WO | 2015/048791 | A1 | 4/2015 |
| WO | 2015/048803 | A2 | 4/2015 |
| WO | 2015/078868 | A1 | 6/2015 |
| WO | 2015/091758 | A1 | 6/2015 |
| WO | 2015/091850 | A1 | 6/2015 |
| WO | 2015/114158 | A1 | 8/2015 |
| WO | 2015/118358 | A1 | 8/2015 |
| WO | 2015114428 | A1 | 8/2015 |
| WO | 2015/163009 | A1 | 10/2015 |
| WO | 2016/087626 | A1 | 6/2016 |
| WO | 2016/087627 | A1 | 6/2016 |
| WO | 2016/141082 | A1 | 9/2016 |
| WO | 2017/022639 | A1 | 2/2017 |
| WO | 2017/161076 | A1 | 9/2017 |
| WO | 2018/222521 | A1 | 12/2018 |
| WO | 2019/224782 | A1 | 11/2019 |
| WO | 2020/120087 | A1 | 6/2020 |
| WO | 2020/193468 | A1 | 10/2020 |

OTHER PUBLICATIONS

Int'l Search Report and Written Opinion dated Jul. 12, 2017 in Int'l Application No. PCT/US2016/056238.

Int'l Search Report and Written Opinion dated Jul. 26, 2013 in Int'l Application No. PCT/US2012/039465.

Int'l Search Report and Written Opinion dated Jul. 31, 2014 in Int'l Application No. PCT/US2014/033598.

Int'l Search Report and Written Opinion dated May 13, 2009 in Int'l Application No. PCT/IL2008/001312.

Int'l Search Report dated Apr. 26, 2010 in Int'l Application No. PCT/US2009/069552.

Int'l Search Report dated Jun. 17, 2011 in Int'l Application No. PCT/US2011/021604.

Int'l Search Report dated Oct. 12, 2011 in Int'l Application No. PCT/US11/21605.

Int'l Search Report dated Sep. 22, 2011 in Int'l Application No. PCT/IL 11/00368; Written Opinion.

Int'l Written Opinion dated Jul. 19, 2012 in Int'l Application No. PCT/US11/21605.

Inte'l Search Report and Written Opinion dated Nov. 30, 2016 in Int'l Application No. PCT/US2016/056223.

International Preliminary Report on Patentability and Written Opinion issued Jul. 5, 2011 in International Application No. PCT/US2009/069552.

Notice of Allowance dated Aug. 24, 2015 in U.S. Appl. No. 29/479,307 by Norton.

(56)    References Cited

OTHER PUBLICATIONS

Offce Action dated Sep. 21, 2010 in U.S. Appl. No. 12/244,666 by Gross.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.
Office Action dated Feb. 4, 2014 in EP Application No. 11 707 942.6.
Office Action dated Jan. 10, 2017 in U.S. Appl. No. 14/193,692, by Gross.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.

Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year: 2021).
English translation of an Office Action dated Jan. 30, 2013 in CN Application No. 200880117084.X.
English translation of an Office Action dated Mar. 5, 2014 in CN Application No. 200880117084.X.
European Search Report (Partial) dated Mar. 8, 2017 in EP Application 16193157.1.
Extended European Search Report dated Aug. 7, 2014 in EP Application No. 1417477.4.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report issued Jul. 28, 2020 in European Application No. 20172466.3.
Extended Search Report dated Aug. 7, 2014 in EP Application No. 14171477.4.
Extended Search Report dated Jul. 7, 2017 in EP Application No. 16193157.1.
Int'l Preliminary Report on Patentability issued Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion issued Jan. 26, 2017 in Int'l Application No. PCT/US2016/056213.
Int'l Search Report and Written Opinion issued Mar. 27, 2017 in Int'l Application No. PCT/US2016/056247.
Int'l Search Report and Written Opinion issued Apr. 21, 2017 in Int'l Application No. PCT/US2016/068367.
Int'l Search Report and Written Opinion issued May 15, 2017 in Int'l Application No. PCT/US2016/068371.
Int'l Search Report and Written Opinion issued Jul. 6, 2017 in Int'l Application No. PCT/US2017/022966.
Int'l Search Report and Written Opinion issued Nov. 28, 2016 in Int'l Application No. PCT/US2016/056218.
Int'l Search Report and Written Opinion issued Dec. 2, 2016 in Int'l Application No. PCT/US2016/056210.
Int'l Search Report and Written Opinion issued Dec. 5, 2016 in Int'l Application No. PCT/US2016/056233.
Int'l Search Report and Written Opinion issued Dec. 8, 2016 in Inl'l Application No. PCT/US2016/056227.
Int'l Search Report and Written Opinion issued Dec. 15, 2016 in Inl'l Application No. PCT/US2016/056258.
Int'l Search Repport (Partial), issued Dec. 20, 2016 in Int'l Application No. PCT/US2016/056247.
Int'l Preliminary Report on Patentability date Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.

(56)          References Cited

OTHER PUBLICATIONS

Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.

Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2013 in IL Application No. 208634.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.
Office Action dated Sep. 6, 2011 in U.S. Appl. No. 12/345,818.
Office Action dated Sep. 9, 2015 in U.S. Appl. No. 13/643,470 by Alon.
Office Action issued Aug. 17, 2021 in Indian Application No. 201827027625.
Office Action issued Feb. 20, 2015 in U.S. Appl. No. 13/521,181 by Cabiri.
Office Action issued Nov. 6, 2015 in U.S. Appl. No. 14/715,791 by Cabiri.
Office Action issued Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
U.S. Appl. No. 13/733,516 by Cabiri, filed Jan. 3, 2013.
U.S. Appl. No. 13/873,335 by Filman, filed Apr. 30, 2013.
U.S. Appl. No. 13/874,017 by Cabiri, filed Apr. 30, 2013.

(56)  References Cited

OTHER PUBLICATIONS

U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.

102  Insert cartridge in arbitrary orientation

103  Activate driver

104  Driver reorient cartridge

106  Cartridge reach locked orientation

108  Cartridge rotationally locked

109  Driver continue to operate

110  Discharge the pharmaceutical

ANTI-ROTATION CARTRIDGE PIN

CROSS-REFERENCE TO RELATED APPLICATIONS

This application is a divisional application of U.S. patent application Ser. No. 16/321,697, filed Jan. 29, 2019, which is a National Phase entry of International Application No. PCT/US16/068065, filed Dec. 21, 2016, which was published Feb. 8, 2018 as International Publication No. WO 2018/026387 A1, which claims the benefit of U.S. Provisional Application No. 62/369,492, filed Aug. 1, 2016, the contents of which are incorporated herein by their entirety.

FIELD AND BACKGROUND OF THE INVENTION

The present invention, in some embodiments thereof, relates a method and system for loading a cartridge into a pharmaceutical device and particularly, but not exclusively, to a system and method for facilitating proper stabilization of the cartridge.

U.S. Pat. No. 8,177,769 relates to "A cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed position, the door coupling element couples the cartridge coupling element with a coupling element of the activation mechanism".

U.S. Pat. No. 7,967,795 relates to "A cartridge interface assembly including a driving plunger including an outer shaft, and a driver including an inner shaft, the inner shaft mating with an intermediate shaft, the intermediate shaft mating with the outer shaft, so that the shafts are movable telescopically with respect to one another, wherein rotation of the driver causes the driving plunger to advance in a direction away from the driver".

U.S. Pat. No. 9,173,997 relates to an apparatus "For administering a substance to a subject. A vial contains the substance and a stopper is disposed within the vial and is slidably coupled to the vial. A first threaded element is (a) rotatable with respect to the vial and (b) substantially immobile proximally with respect to the vial during rotation of the first threaded element. A second threaded element is threadably coupled to the first threaded element. At least a distal end of the second threaded element is substantially non-rotatable with respect to the vial, and the distal end of the second threaded element defines a coupling portion that couples the second threaded element to the stopper. The first threaded element, by rotating, linearly advances the stopper and at least the distal end of the second threaded element toward a distal end of the vial. Other embodiments are also described."

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to an aspect of some embodiments of the invention, there is provided a system for loading pharmaceutical into a pharmaceutical delivery device including: a cartridge including a cylindrical reservoir having a longitudinal axis and containing the pharmaceutical; a cartridge bay in the pharmaceutical delivery device, the bay sized and shaped to receive the cartridge with the cylindrical reservoir rotated in any of a first orientation and a second orientation rotated around the longitudinal axis; a first interference element on the cartridge and a second complementary interference element on the delivery device, wherein the first interference element on the cartridge and a second complementary interference element are disengaged when the cartridge is fully received by the bay and the reservoir is in any of the first orientation and the second orientation; the first interference element and second complementary interface element interlocking when the cartridge is fully loaded into the bay and the cartridge is in a third orientation around the longitudinal axis, the interlocking preventing rotation of the reservoir around the longitudinal axis in at least one direction.

According to some embodiments of the invention, in the cartridge fits into the bay by longitudinal insertion.

According to some embodiments of the invention, the first interference element is located on a leading face of the cartridge.

According to some embodiments of the invention, the complementary interference element contacts the cartridge only when the cartridge is more than 97% inserted into the bay.

According to some embodiments of the invention, the complementary interference element is longitudinally displaced by the cartridge after the cartridge is inserted into the bay at least 97% of its full insertion.

According to some embodiments of the invention, in the first orientation the first interference element and the second complementary interference element overlap in and at least one element of the first interference element and the second complementary interference element is configured for elastically displacing to accommodate the overlap.

According to some embodiments of the invention, when the at least one element is configured to apply a resistance to insertion of the cartridge into the cartridge bay as a result of the elastically displacing.

According to some embodiments of the invention, the system further includes a lock configured for counteracting the resistance.

According to some embodiments of the invention, the lock includes a latch.

According to some embodiments of the invention, in the first orientation the first interference element and the second complementary interference element are disengaged facilitating rotation either direction around the longitudinal axis with respect to the delivery device around.

According to some embodiments of the invention, in the third orientation the interlocking of the first interference element and the second complementary interference element inhibits rotation of the cartridge around the longitudinal axis with respect to the delivery device in two opposite directions.

According to some embodiments of the invention, the system further includes a driver for imparting a torque between the pharmaceutical delivery device and the cartridge around the longitudinal axis.

According to some embodiments of the invention, the driver is configured to drive discharge of the pharmaceutical when the cartridge is prevented from rotating around axis in the at least one direction.

According to some embodiments of the invention, the driver includes a threaded element.

According to some embodiments of the invention, the drive pushes a plunger axially inside of the cylindrical reservoir.

According to some embodiments of the invention, the driver includes a telescoping screw assembly.

According to some embodiments of the invention, the driver applies the torque to the threaded element and the threaded element is threadably connected to a second threaded element and the second threaded element is inhibited from rotating around the longitudinal axis with respect to the cartridge.

According to an aspect of some embodiments of the invention, there is provided a method of loading a pharmaceutical cartridge having a cylindrical reservoir into a delivery device including; inserting the cartridge longitudinally into a cartridge bay of the delivery device in a first orientation; applying a torque to the cartridge with a driver; reorienting the cartridge to a second orientation around a longitudinal axis of the reservoir as a result of the applying a torque; interlocking an interference element on the cartridge to a complementary interference element on the delivery device to lock the cartridge in the second orientation; discharging a pharmaceutical from the cartridge as a result of continuing the applying and the interlocking.

According to some embodiments of the invention, the method further includes: elastically displacing an interference element as a result of the inserting; at least partially releasing the elastically displacing when the cartridge reaches the second orientation.

According to some embodiments of the invention, the elastically displacing produces a resistance to the inserting and further including: fixing the cartridge in the cartridge bay after the elastically displacing and wherein the fixing at least partially counteracts the resistance.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
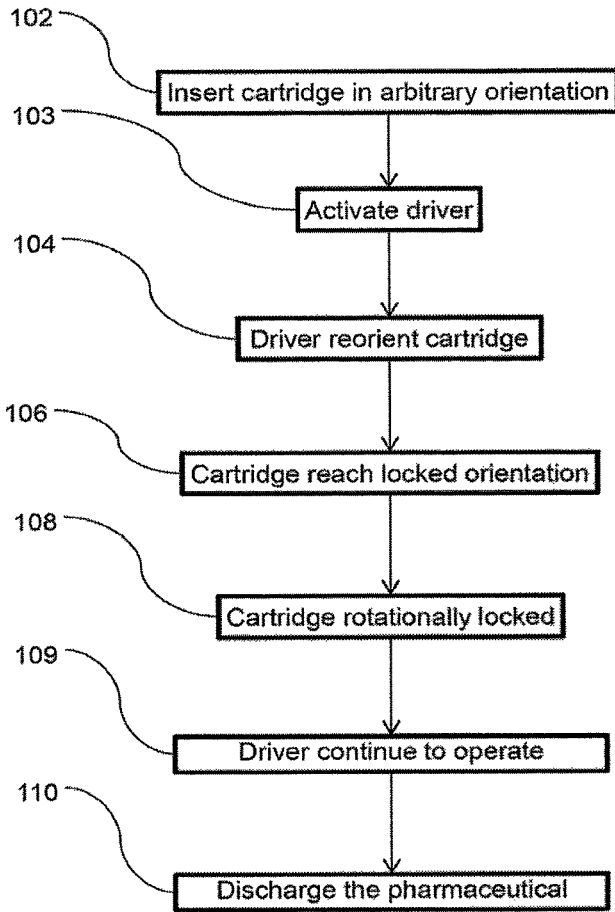
FIG. 1 is a flow chart of illustration of inserting and/or orientating and/or locking a cartridge in accordance with an embodiment of the current invention.

The present invention, in some embodiments thereof, relates a method and system for loading a cartridge into a pharmaceutical device and particularly, but not exclusively, to a system and method for facilitating proper stabilization of the cartridge.

Overview

An aspect of some embodiments of the current invention relates to system for stabilizing a pharmaceutical cartridge into a fixed orientation. The cartridge stabilization system optionally allows introduction of a cartridge into a cartridge bay in either the locked orientation and/or another orientation and/or reorients the cartridge to the locked orientation and/or stabilization the cartridge in the locked orientation.

In some embodiments, a stabilization system will be configured to avoid interference with insertion of a cartridge. For example, the stabilization system may allow insertion of the cartridge in a locked orientation and/or in another orientation and/or in an arbitrary orientation.

In some embodiments, the mechanism by which the cartridge is locked will not apply against the insertion of the cartridge. For example, for a longitudinally inserted cartridge, an interference force may resist rotation around the longitudinal axis, but not longitudinal movement. Alternatively, or additionally the force of the locking mechanism may resist insertion only in a portion of the insertion trajectory. For example, resistance to insertion may be at the beginning or end of the insertion process. Optionally, the force resisting insertion may be less than $\frac{1}{100}$ the force resisting the locking direction and/or the insertion resistance may range between $\frac{1}{100}$ to $\frac{1}{50}$ of the force of locking, and/or the insertion resistance may range between $\frac{1}{50}$ to $\frac{1}{10}$ of the force of locking, and/or the insertion resistance may range between $\frac{1}{10}$ to $\frac{1}{2}$ of the force of locking. For example, a resistance to insertion may be applied to less than $\frac{1}{2}$ of the insertion trajectory and/or over less than $\frac{1}{4}$ of the insertion trajectory and/or less than $\frac{1}{8}$ of the insertion trajectory and/or less than $\frac{1}{20}$ of the insertion trajectory.

In some embodiments, a cartridge stabilization system may assist cartridge insertion. For example, a cartridge stabilization system may add a resistance force that stops when a cartridge is fully inserted into a pharmaceutical delivery device. For example, the stabilization system may serve as a tactile indication to a user indicating that the cartridge is fully installed. For example, the interference element may exert a force ranging between 200 to 400 g and/or between 400 to 800 g and/or between 800 to 2000 g when it is deflected. For example the interference element may deflect between 0.5 to 1.0 mm and/or between 1.0 to 1.5 mm and/or between 1.5 to 3 mm. For example the ratio between the force and/or distance of deflection of the interference element when it interlocks to a complementary interference element to the force and/or distance of deflection when the interference element overlaps the complementary interference element may range between 0 to 0.3 and/or between 0.3 to 0.6 and/or between 0.6 to 0.9 and/or between 0.9 to 1.0. Optionally, the interlocked interference elements may hold a cartridge immobile and/or stable for a torque ranging between 0 to 200 g-cm and/or between 0 to 500 g-cm and/or between 0 to 1000 g-cm. In some embodiments the axial force developed by a driver on a plunger, for example during pharmaceutical delivery ranges between 0.5 to 2 kg and/or between 2 to 4 kg and/or between 4 to 10 kg.

In some embodiments, the cartridge is reoriented to a final and/or locked position after insertion. Optionally, a driver, which drives delivery of a pharmaceutical, will also drive reorientation of a cartridge. For example, a drive may apply a torque to a cartridge. The torque my reorient the cartridge until the stabilization system stabilizes the cartridge in the locked orientation. Optionally, when the cartridge is locked, the driver may begin continue to drive the cartridge.

Optionally, after locking the force of the driver may perform a different function from reorienting. For example, once the cartridge is locked and/or resists rotation, the torque of the driver may be converted into a force discharging and/or delivering the pharmaceutical and/or drive a preparation for discharge, for example pushing a plunger driver and/or a plunger and/or piercing a septum.

In some embodiments, a locking mechanism includes an interference element.

Optionally, the interference element does not interfere with movement when the cartridge is not in the locked position. Alternatively or additionally, the interference element may be elastically pushed out of a locking position when the cartridge is not in a locked position. Alternatively or additionally, an interference element will produce a force in one direction (for example, a resistance to insertion due to friction and/or elastic forcing of the interference element) while the cartridge is out of the locked position and/or the interference element will produce a different force (for example blocking rotation) in the locked position. In some embodiments, the non-locking positions may include for example angles covering between 359 to 300 degrees of orientations and/or between 300 to 200 degrees and/or between 200 to 100 degrees and/or between 100 to 50 degrees and/or between 50 to 2 degrees.

In some embodiments, a cartridge will include an interference element on a leading face and/or surface thereof (a leading face and/or surface may include a surface that is facing the direction of travel as the cartridge is inserted into the delivery device). For example, for a cartridge that is optionally pushed distally into a cartridge bay the interference element may optionally be located on a distal face of the cartridge. Optionally, the interference element does not interlock with a complementary element and/or does not interfere with insertion of the cartridge until the distal face is inserted to reach a complementary interference element of the delivery device. For example, the interference elements may interact in an area ranging between the last ½ to the last ⅒ of the insertion and/or between the last ⅒ to the last ¹⁄₁₀₀ of the insertion. For example, the interference elements may interact in an area ranging between the last 2 cm to the last 4 mm of the insertion and/or between the last 4 mm to the last 0.4 mm of the insertion.

In some embodiments, a driver includes an antirotational connection to a pharmaceutical reservoir. For example, a plunger and/or a friction pad may supply antirotational friction between an inner wall of a reservoir and the driver.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flow Chart of an Exemplary Method of Stabilizing a Cartridge

FIG. 1 is a flow chart illustration of inserting and/or orientating and/or locking a cartridge in accordance with an embodiment of the current invention. In some embodiments, a user inserts 102 a pharmaceutical cartridge into a delivery device in an arbitrary orientation. Optionally, the device reorients 104 the cartridge until it reaches a locked orientation 106 and locks 108. For example, the driver that drives discharge 110 of the pharmaceutical also drives orientation of the cartridge.

In some embodiments, a user inserts 102 a pharmaceutical cartridge into a delivery device. For example, a pharmaceutical cartridge may include a tubular reservoir that is inserted longitudinally into a cartridge bay. For example, a cartridge may include a syringe and/or a vial and/or an ampoule. In some embodiments, during delivery the cartridge may be stabilized in the cartridge bay at a fixed orientation. Nevertheless, it may be desirable that the device perform properly when the user inserts 102 the cartridge in an arbitrary orientation. Furthermore, it may be desirable that the locking mechanism not impede cartridge insertion. For example, a friction based stabilization may impede insertion of the cartridge. Optionally, the cartridge is inserted 102 while the locking mechanism is disengaged.

In some embodiments, a user initiates the device. For example, initiating the device may include activating 103 a driver of pharmaceutical delivery. Optionally, initially, for example while the cartridge in unlocked, the driver may not drive delivery of the pharmaceutical. For example, initially, the driver may drive reorientation 104 of the cartridge. Optionally, the cartridge will continue to reorient 104 until it reaches a locked orientation 106 and/or is locked 108.

In some embodiments, a delivery driver will continue to operate 109 after a cartridge is locked 108 and/or in its locked orientation 106. Optionally, continued operation 109 of the driver discharges 110 the pharmaceutical and/or delivers the pharmaceutical to a subject.

Embodiments of a Cartridge Stabilizer

Figure 2A:
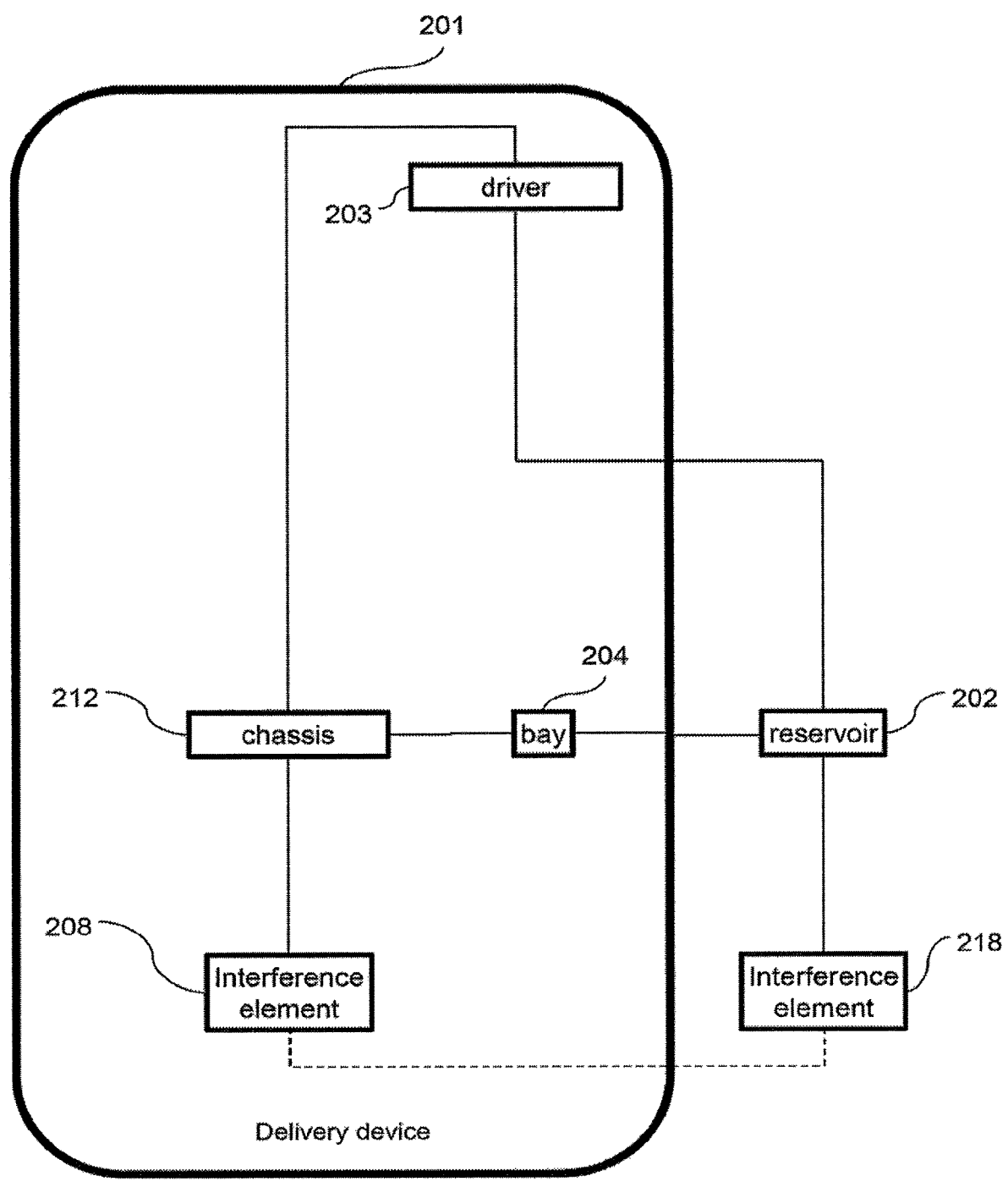
FIGS. 2A and 2B are a block diagram of illustrations of cartridge stabilization systems in accordance with embodiments of the current invention.

FIG. 2A is a block diagram of illustration of cartridge stabilization system in accordance with an embodiment of the current invention. In some embodiments, a delivery device 201 includes a cartridge bay 204 that accommodates a pharmaceutical reservoir 202. For example, bay 204 may accommodate reservoir 202 in more than one possible orientation. Optionally, when reservoir 202 is in a locked orientation, complementary interference elements 218 and 208 on the cartridge and bay respectively interlock and/or lock the cartridge into the locked orientation. Optionally, when the cartridge is in a non-locked orientation, interference elements 218 and 208 overlap. Optionally, when the cartridge is in a non-locked orientation at least one of interference elements 218 and 208 is elastically displaced.

In some embodiments, delivery device 201 includes a driver 203. Optionally driver 203 drives reorientation of reservoir 202 in bay 204. For example, driver 203 may produce a torque that rotates reservoir 202. Optionally, the torque may reorient cartridge, for example by rotating reservoir 202 around an axis inside bay 204. Optionally, when reservoir 202 reaches a particular orientation (for example a locked orientation), interference element 218 on the cartridge interlocks with interference element 208 on the delivery device and/or stops reorientation of the cartridge with respect to the device.

In some embodiments, when reservoir 202 is locked, further torque of driver 203 drives delivery of the pharmaceutical. For example, reservoir 202 may include a pharmaceutical reservoir and/or a pump for discharging a pharmaceutical from the reservoir. For example, driver 203 may impel a plunger into the reservoir to discharge the pharmaceutical from reservoir 202.

In some embodiments, driver 203 may include a telescoping screw assembly (TSA) and/or a plunger interface. For example, driver 203 may include a motor (for example a DC electric motor and/or a brushless electric motor and/or a chemical powered motor). The motor optionally applies a torque between the TSA and a chassis 212 of the delivery device. Optionally the TSA applies the torque to the plunger; the plunger optionally applies the torque to the reservoir. For example, as long as reservoir 202 is free to rotate, the torque of the motor rotates reservoir 202. When reservoir 202 is locked by interlocked interference elements 208 and/or 218, to the cartridge produces a counter torque, which is transmitted to the TSA. Optionally the torque and counter torque on the TSA may cause screw threads in the TSA to rotate with respect to each other expanding the telescoping assembly and/or driving the plunger and/or discharging the pharmaceutical. Alternatively or additionally, a driver may include a linear actuator and/or a piston assembly, which drives discharge. Alternatively or additionally, torque may be transferred between the cartridge and the driver by friction between the plunger and the inner wall of the reservoir and/or by a friction element (for example a friction pad contacting and inner wall of the reservoir) and/or by an interference element.

Figure 2B:
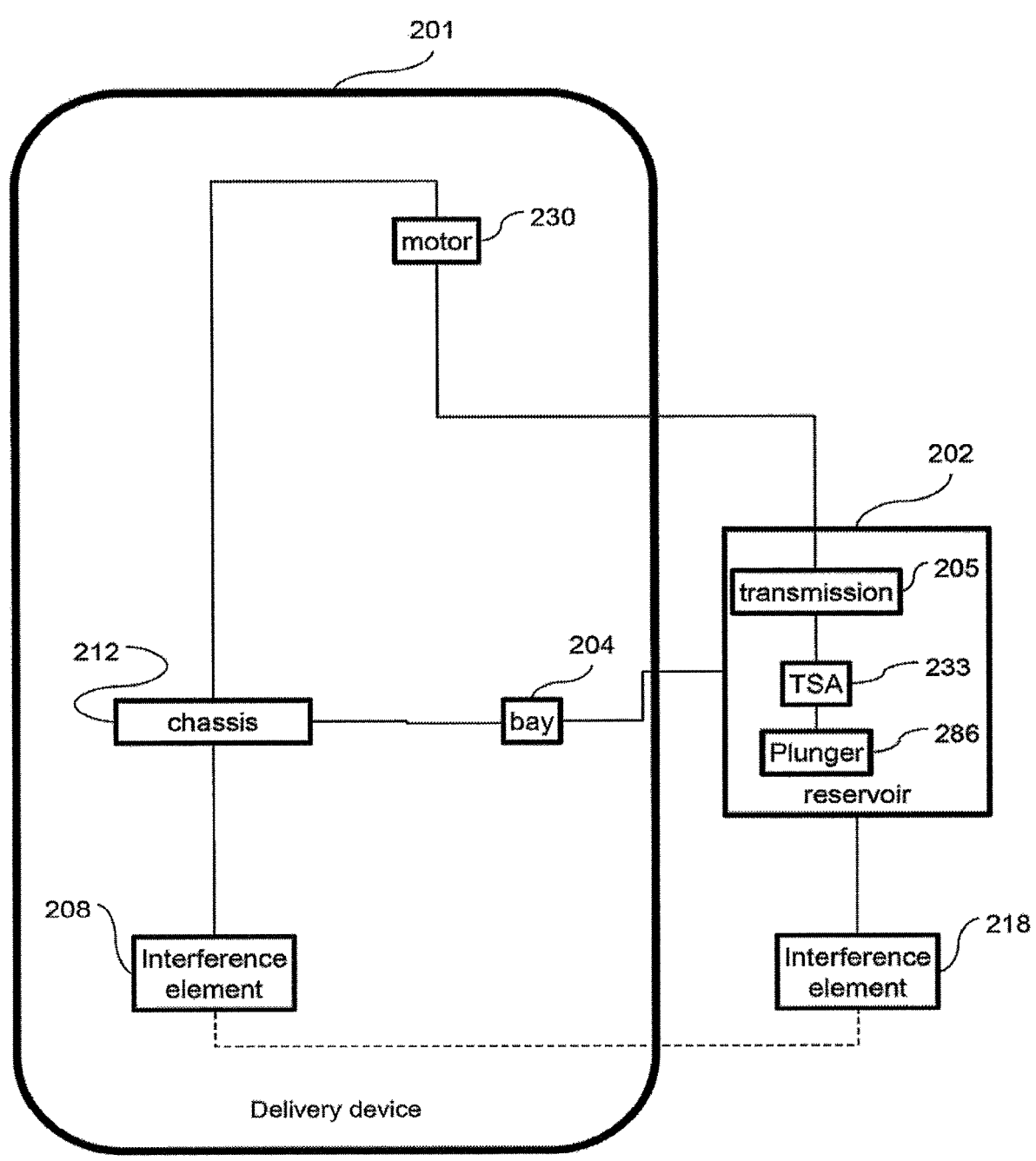

FIG. 2B is a block diagram illustrating and alternative pharmaceutical delivery device in accordance with an embodiment of the current invention. In some embodiments, a drug delivery device 201 may include a motor 230. Optionally, motor 230 drives a transmission 205. For example, transmission 205 may transmit rotational energy to a telescoping screw assembly, TSA 233. Optionally TSA 233 is connected to a plunger 286 of a reservoir 202. For example, torque from motor 230 may rotate an entire cartridge (for example including transmission 205, TSA 233, plunger 286 and/or reservoir 202). Alternatively or additionally, when reservoir 202 and/or plunger 286 are prevented from rotating, rotating transmission 205 may rotate on part of TSA 233 with respect to a threadably connected second part of TSA 233. Rotation of the threadably connected parts with respect to one another optionally expands TSA 233 and/or pushes plunger 286 into the reservoir, for example driving discharge of a pharmaceutical.

Exemplary Surfaces of Contact with a Cartridge

FIGS. 3A-3D are schematic illustrations of a cartridge stabilization system in accordance with an embodiment of the current invention. Optionally, a cartridge may include a cylindrical reservoir 302, which is inserted longitudinally into a delivery device in an arbitrary orientation. Cylindrical reservoir 302 optionally is free to rotate until an interference element 308 of the delivery device interlocks with a complementary feature on the cartridge inhibiting further rotation of the cartridge with respect to the delivery device.

Figure 3A:
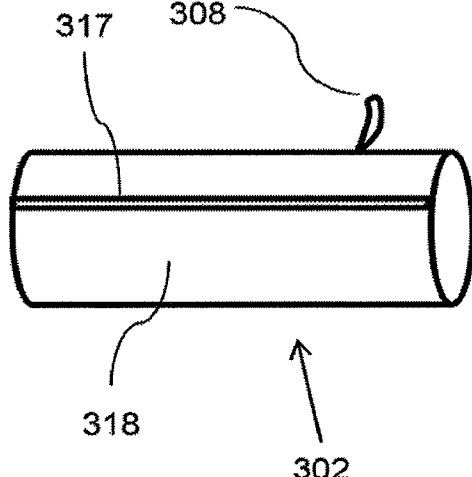
FIGS. 3A-3D are schematic illustrations of a cartridge stabilization system in accordance with an embodiment of the current invention.
Figure 3B:
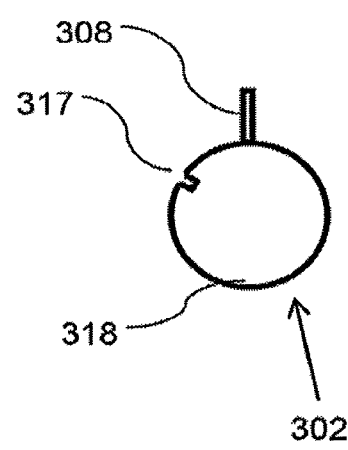

In some embodiments, reservoir 302 includes a groove 317 and/or a complementary interference element, for example a protruding section 318 configured to interlock with an interference element 308 on the delivery device. Optionally, interference element 308 is elastic. For example when groove 317 is not aligned with interference element 308 and/or when protruding section 318 overlaps interference element 308 (for example as illustrated in FIGS. 3A and 3B) then element 308 may flex out of the way of cartridge 302 allowing insertion of cartridge 302 into the delivery device and/or allowing rotation of cartridge 302 with respect to the delivery device.

Figure 3C:
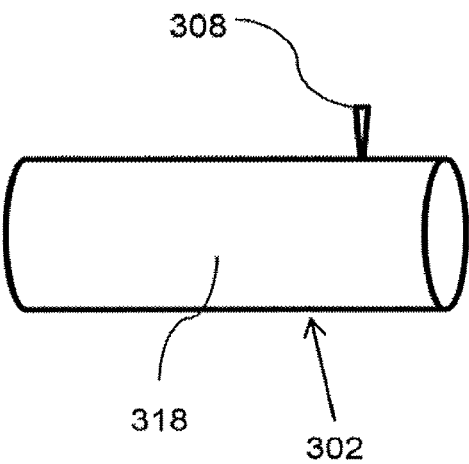
Figure 3D:
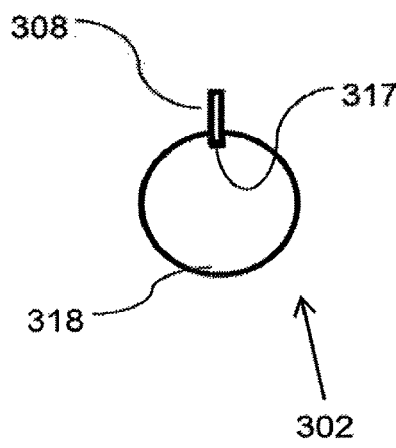

In some embodiments, when groove 317 is aligned with element 308, then element 308 and protruding section 318 interlock. For example, element 308 may be biased toward groove 317 such that when they are aligned element 308 snaps into groove 317 and/or interlocks (for example as illustrated in FIGS. 3C and/or 3D). Optionally, interlocking may allow longitudinal movement of the cartridge with respect to the device. Optionally, interlocking may inhibit further rotation of cartridge with respect to the device.

Figure 4A:
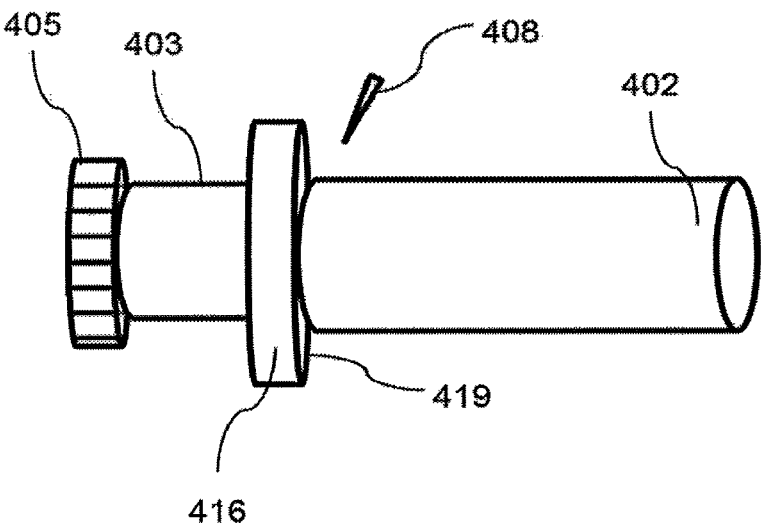
FIGS. 4A and 4B are schematic illustrations of an alternative cartridge stabilization system in accordance with an embodiment of the current invention.
Figure 4B:
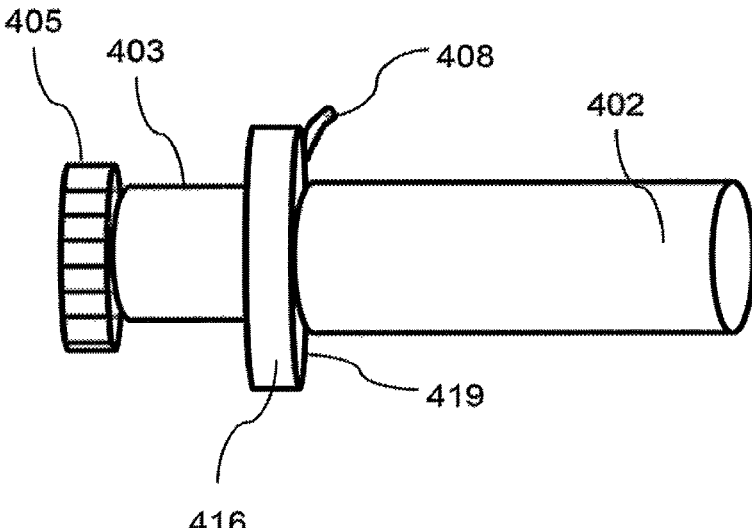

FIGS. 4A and 4B are schematic illustrations of an alternative cartridge stabilization system in accordance with an embodiment of the current invention. In some embodiments, a cartridge includes a complementary interference element on a leading face of the cartridge. For example, the cartridge may be inserted distally into a cartridge bay. The complementary interference element of the cartridge may be on a distal face of the cartridge. For example, the distal face may encounter an interference element of the delivery device when as the cartridge approaches complete insertion into the delivery device. Optionally, the interference elements will not inhibit (and/or affect) the beginning of cartridge insertion.

In some embodiments, a cartridge may include a reservoir 402 having a proximal flange 416. Optionally, an interference element 408 on the delivery device interacts with a complementary element on the cartridge. For example, the distal face 419 of flange 416 may include a groove and/or a protrusion that interlocks with element 408 when cartridge is in a particular orientation. For example, when element 408 overlaps with the protrusions either element 408 or the protrusion may be elastically displaced. For example, when element 408 is aligned with the groove it may snap into the groove and/or interlock with the protrusion and/or lock the orientation of reservoir 402. Optionally, element 408 will contact flange 416 during the last 1 mm of cartridge insertion. For example, at the end of insertion, elastic forces of element 408 may push the cartridge outward from the cartridge bay until the cartridge reaches a fully in inserted position. At the fully inserted position, the cartridge may be fixed in place, fixing the cartridge may include an opposing force to the outward force of element 408. For example, the resistance force of element 408 and/or the nullification of the resistance may serve as a tactile sign to the user that the cartridge has been fully inserted.

In some embodiments, a cartridge includes a TSA 403. For example, TSA 403 may be connected to a transmission, for example including a drive gear 405.

Optionally, when the cartridge is inserted into the delivery device, the transmission connects to a motor that drives TSA to rotate the cartridge and/or to discharge the pharmaceutical.

Exemplary Stabilizing of a Cartridge and/or Discharging of a Pharmaceutical

Figure 5:
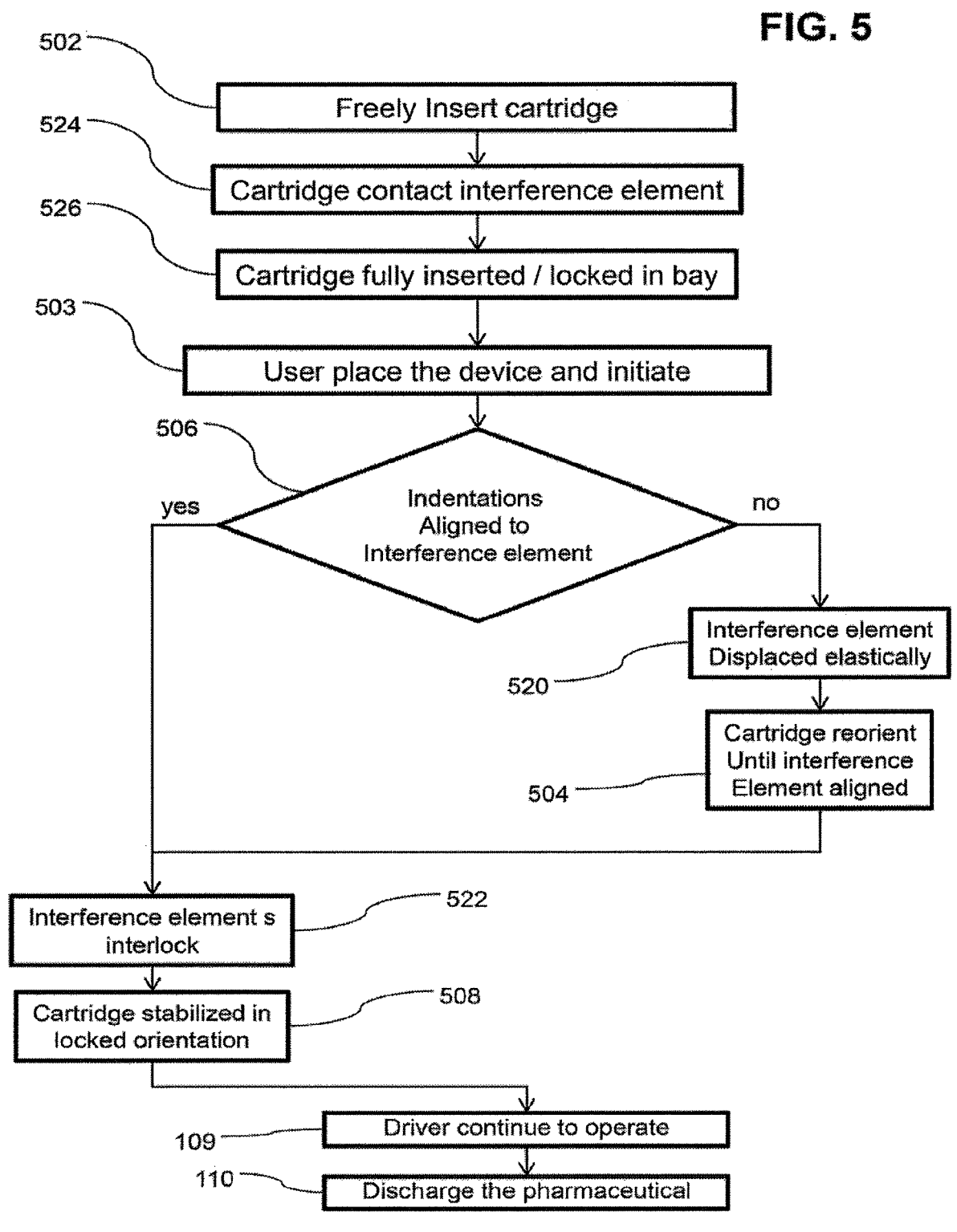
FIG. 5 is a flow chart of illustration of inserting and/or orientating and/or locking a cartridge in accordance with an embodiment of the current invention.

FIG. 5 is a flow chart of illustration of inserting and/or orientating and/or locking a cartridge in accordance with an embodiment of the current invention. In some embodiments, the locking mechanism does not affect cartridge insertion until the cartridge is close to the end of insertion. At the end of insertion, the interference element of the delivery device optionally contacts a complementary surface and/or element of the cartridge. For example, the complementary surface may be a surface with a portion that interlocks to the interference element and/or a portion that facilitate reorientation of the cartridge until an interlocking portion of the surface contacts the interference element.

In some embodiment, a cartridge is freely inserted 502 into a delivery device.

Optionally, the cartridge may be inserted 502 in various and/or arbitrary orientations. For example, for a cartridge with a cylindrical reservoir, the cartridge optionally is inserted in any rotational orientation around the longitudinal axis of the reservoir. Optionally, a stabilization system does not interfere with insertion at least for insertion to between 50 to 90% and/or between 90 to 97% and/or between 97 to 99% of its fully inserted depth. For example, the stabilization system may not interfere with the orientation of the cartridge and/or apply a force to the cartridge before it is inserted to the stated depth. Alternatively or additionally, the stabilization system may apply an average force over the beginning portion of insertion that is less than ½ and/or less than ¹⁄₁₀ and/or less than ¹⁄₁₀₀ the average force over the final portion of insertion.

In some embodiments, the cartridge may contact 524 an interference element of a stabilization system during a final portion of insertion after an initial portion of insertion. For example, the initial portion of insertion may range between 50% inserted to 90% inserted and/or between 90% to 95% and/or between 95% to 99% and/or greater than 99% of the fully inserted depth. For example, after the cartridge contacts 524 the interference element, the element may produce resistance to further insertion and/or an outward force. For example, the outward force may push the cartridge out from the cartridge bay. Optionally, when the cartridge is fully inserted it may be fixed 526 in the cartridge bay. For example, the fixing 526 may counteract and/or nullify the outward force of contact 526 with the interference element.

Optionally, the resistance resulting from contact 524 with the interference element may serve the user as a sign that the cartridge is approaching full insertion and/or has not reached full insertions. Optionally, fixing 526 may serve the user as a sign that the cartridge is properly and/or fully inserted.

In some embodiments, after a cartridge is fully inserted 502 and/or fixed 526, a user may place the pharmaceutical delivery device onto a delivery site and/or activate 503 the device. Optionally, when the device is active and the cartridge is in a non-locked orientation [no in decision box 506] (for example, an interference element in the cartridge bay in not aligned and/or not interlocking with a complementary feature on the cartridge and/or an interference elements on the delivery device overlaps an interference element on the cartridge) then one of the interference element may be displaced elastically 520. For example, elastic displacement 520 may be by elastic deformation of the interference element and/or the interference element may have an elastic mount (for example a spring and/or an elastic joint) that deforms elastically. For example, the displacement may be caused by overlap of the interference element with a complementary interference element. Optionally, when the cartridge is in a non-locked orientation [no in decision box 506], action of a driver on the cartridge may reorient 504 (for example rotate) the cartridge. Optionally, the driver continues to reorient 504 the cartridge with respect to the delivery device until the cartridge reaches the locked orientation.

In some embodiments, when the cartridge is in a locked orientation [yes in decision box 506], an interference elements on the cartridge and/or delivery device may interlock 522. Interlocking 522 may orientationally lock 508 the cartridge in the locked orientation. Optionally, when the cartridge is orientationally locked 508, the driver may continue to operate 109. For example, continued operation 109 of the driver when the cartridge in orientationally locked 508 may cause delivery and/or discharge 110 of the pharmaceutical.

Detailed Embodiments of a Cartridge Stabilizing System

Figure 6:
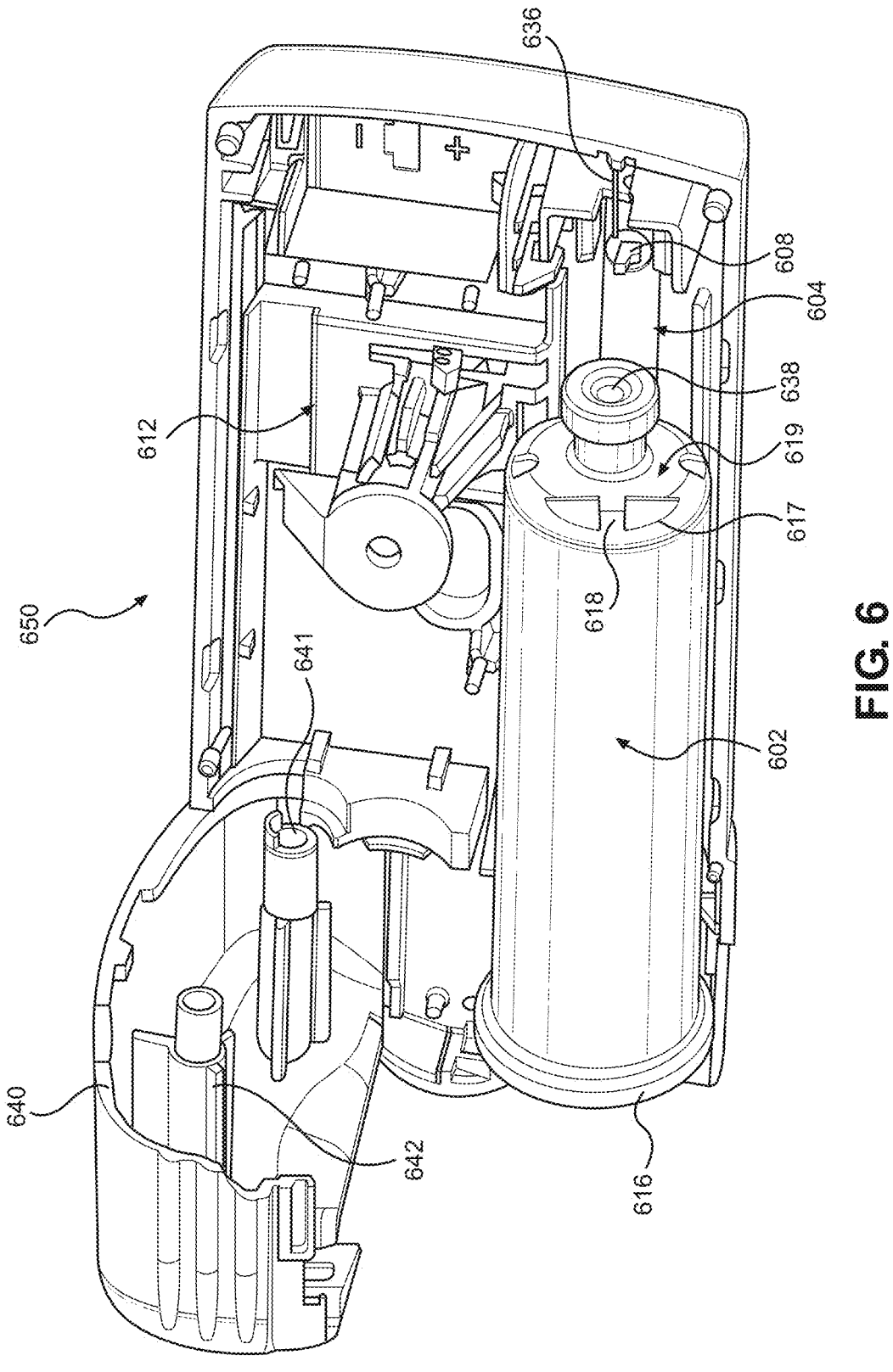
FIG. 6 is a perspective cut-away illustrations of a pharmaceutical delivery device including a cartridge stabilization system in accordance with an embodiment of the current invention.

FIG. 6 is a perspective cut-away illustration of a pharmaceutical delivery device including a cartridge stabilization system in accordance with an embodiment of the current invention. In some embodiments, a reservoir fits into a cartridge bay. As reservoir is inserted, a leading face optionally contacts an interference element of the delivery device. Optionally, in some orientations, a protrusion on the leading face contacts the interference element and/or elastically displaces the interference element.

Optionally, in some orientations, a depression on the leading face contacts the interference element. For example, a depression and/or a protrusion may include a complementary interference element that optionally interlocks with the interference element of the delivery device and/or locks the orientation of reservoir.

In some embodiments, when a reservoir is almost fully inserted, an interference element 608 of the delivery device contacts a leading face 619 including complementary element 618. For example, face 619 may include protrusions and/or depressions 617 (for example, a complementary interference element 618 may include a protrusion in face 619). When interference element 608 contacts face 619, element 608 is elastically displaced. For example, when element 608 contacts face 619, element 608 bends distally. Optionally, displacing element 608 causes resistance to cartridge insertion. In some embodiments, inserting the reservoir further after contacting element 608, further displaces element 608 and/or activates a longitudinal fixing mechanism that fixes the cartridge in the cartridge bay.

In some embodiments, a reservoir 602 of the cartridge includes a connector. For example, reservoir 602 includes a septum 638. Optionally, the delivery device 650 includes a complimentary connector, for example, a hollow needle 636.

Optionally, as the cartridge reaches its locked position needle 636 punctures septum 638 and creates a fluid path between reservoir 602 and the delivery device 650.

In some embodiments, the pharmaceutical delivery device 650 includes a closure element. For example, the pharmaceutical delivery device 650 may include a door 640 to the cartridge bay 604. For example, the door 640 rotates around an axle 641 to open and/or close.

In some embodiments, a closure element, for example door 640 may includes parts of a driver of the delivery device. For example, door 640 includes a second axle 642, which optionally supports a connection between the cartridge and the delivery device 650. For example, the connection may include a gear that connects a TSA of the cartridge to a motor 25 of the delivery device 650. An exemplary drive system of device 650 and/or reservoir 602 is shown, for example, in more detail in FIG. 7.

In some embodiments, a cartridge includes a flange 616. For example, a latch in device 650 may block flange 616 when reservoir 602 is fully inserted into bay 604 and/or longitudinally fix reservoir 602 into bay 604.

Figure 7:
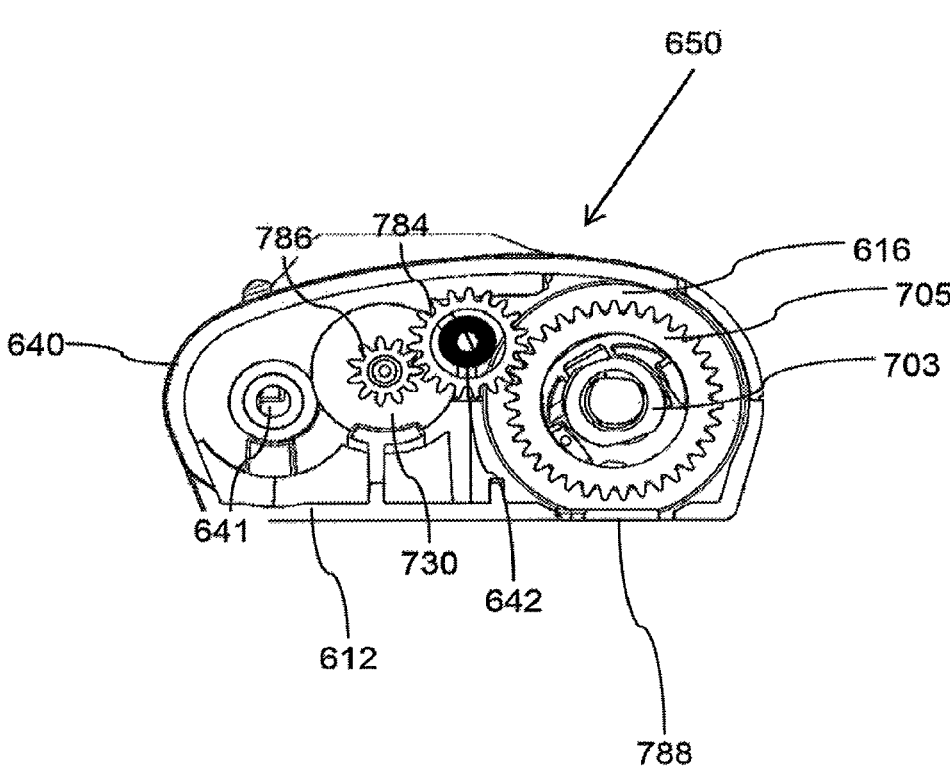
FIG. 7 is a schematic proximal cut-away illustration of a pharmaceutical delivery device including a cartridge stabilization system in accordance with an embodiment of the current invention.

FIG. 7 is a schematic proximal cross sectional illustration of pharmaceutical delivery device 650 including a cartridge stabilization system in accordance with an embodiment of the current invention. In some embodiments, delivery device 650 includes a motor 730. For example, motor 730 is connected by a transmission 705 to a TSA 703. Optionally, when motor 730 is connected to TSA 703, motor 730 rotates TSA 703.

In some embodiments, a motor 730 is mounted to chassis 612 of the delivery device 650. Optionally, motor 730 rotates a gear 786 with respect to chassis 612. Another gear 784 is optionally mounted on axle 641 of door 640. For example when door 640 is closed (for example as illustrated in FIG. 7), gear 784 interconnects between gear 786 and transmission 705. Optionally, when gear 786 is connected to transmission 705, rotating gear 786 causes TSA 703 to rotate with respect to chassis 612.

In some embodiments, TSA 703 is rotationally interlocked to reservoir 602.

Optionally, when reservoir 602 can rotate with respect to chassis 612 then rotating transmission 705 rotates reservoir 602. Alternatively or additionally, when reservoir 602 is rotationally locked with respect to chassis 612, then rotating transmission 705 rotates one end of TSA 703 with respect to the other end of TSA 703. Rotating one end of TSA 703 with respect to the other end of TSA 703 optionally causes TSA 703 to expand or contract. For example, expanding TSA 703 may push a plunger into the reservoir and/or discharge a pharmaceutical.

In some embodiments, a latch 788 fixes the cartridge into bay 604. For example, when the cartridge is inserted into bay 604, latch 788 flexes downward to allow flange 616 to enter bay 604. Alternatively or additionally, when the cartridge it's fully inserted into bay 604, latch 788 snaps upward, blocking flange 616 into position and/or fixing the cartridge inside bay 604. Optionally, latch 788 produces a counter force at least partially negating the resistance to insertion of the elastic displacement of interference element 608.

Figures 8A, 8B:
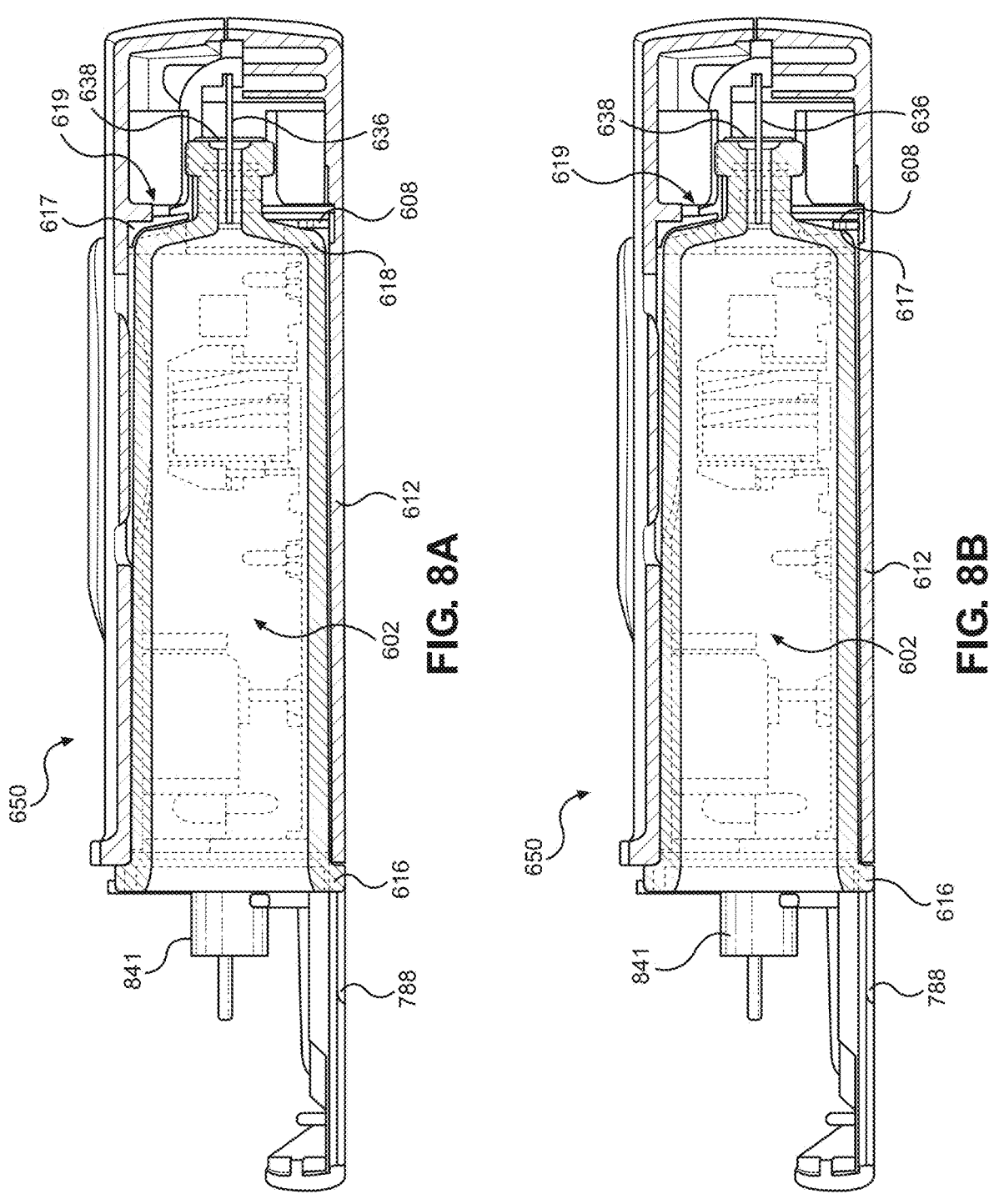
FIGS. 8A and 8B are perspective cut-away illustrations of a pharmaceutical delivery device including a cartridge stabilization system in accordance with an embodiment of the current invention.

FIGS. 8A and 8B are perspective cut-away illustrations of pharmaceutical delivery device 650 including a cartridge stabilization system in accordance with an embodiment of the current invention. In some embodiments, when leading face 619 of a cartridge contacts interference element 608, the face 619 and/or the interference element 608 may be elastically displaced. Optionally, elastic displacement may occur when an interference element 618 on the cartridge is interlocks with a complementary element 608 on the delivery device 650, for example when interference element 608 overlaps an indentation 617 on face 619. Alternatively or additionally, elastic displacement may occur when an interference element 618 on the cartridge is not aligned with a complementary element 608 on the delivery device, for example, when interference element overlaps with a projection. The elastic displacement force may give a tactile feedback to a user helping him know when the cartridge has been completely inserted. In some orientations, the elements 608 and/or 618 may stabilize the orientation of the cartridge.

FIG. 8A illustrates an exemplary embodiment of the current invention with a reservoir 602 fully inserted into a bay 604. In FIG. 8A reservoir 602 is optionally oriented such that interference elements 608 and 618 are not aligned. For example, interference element 608 may overlap and/or be elastically displaced by a protrusion on face 619 of the cartridge. In some embodiments, when reservoir 602 is fully inserted into bay 604 a latch 788 fixes flange 616 into the delivery device.

In some embodiments, a protrusion on leading face 619 of reservoir 602 pushes interference element 608 and/or elastically displaces element 608. Element 608, optionally, forces reservoir 602 backwards giving a tactile resistance to the user.

Optionally, when interference element 608 is not aligned with interference element 618, reservoir 602 is free to rotate around its axis.

In some embodiments, a driver, for example TSA 703 causes the reservoir 602 to rotate. Optionally, reservoir 602 rotates until interference element 608 is aligned with interference element 618. Alternatively or additionally, reservoir 602 may be inserted into bay 604 in an orientation with interference elements 608 and 618 already aligned.

In some embodiments, for example, as Illustrated in FIG. 8B, when interference element 608 is aligned with element 618, then interference element 608 snaps into a groove and/or indentation 617 of face 619 and/or interlocks with a complementary interference element 618 and/or locks the orientation of reservoir 602.

Optionally, interference element 608 is less displaced or not all displaced when it is aligned with element 618 than when it overlaps element 618. For example, when the interference elements are aligned the elastic displacement and/or elastic force may range between 50% to 90% the displacement when the elements are not aligned (for example when they overlap) and/or between 20% to 50% and/or between 1% to 20% and/or when aligned there may be no elastic displacement of the interference elements and/or not elastic force between the cartridge and the delivery device.

In some embodiments, when reservoir 602 is fully inserted into bay 604, a connection and/or a fluid path may be created between reservoir 602 and delivery device 650. For example, a hollow needle 636 may puncture a septum 638 of a reservoir 602. Optionally, puncturing septum 638 may create a fluid path between device 650 and reservoir 602. Illustrated, for example, in FIGS. 8A and 8B is a hinge 841 of device 650 around which hinge 641 and/or door 640 revolve.

Figures 9A, 9B:
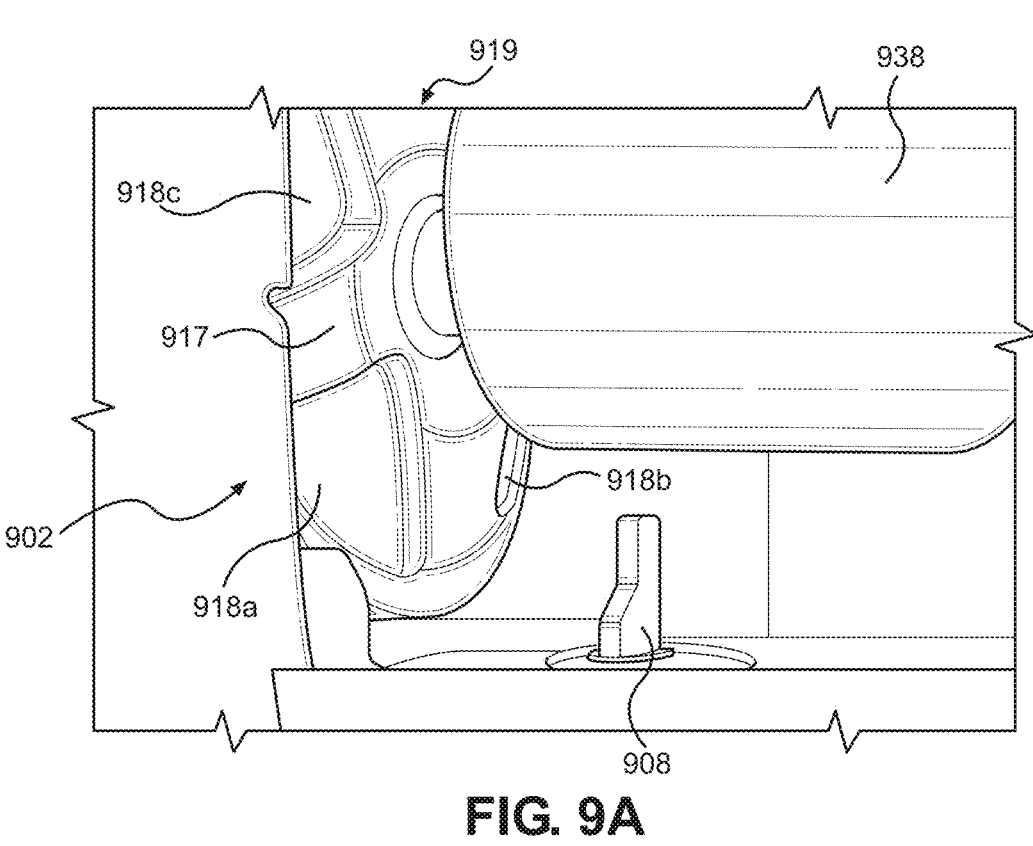
FIGS. 9A-9C illustrate a cartridge stabilization system in accordance with an embodiment of the current invention.
Figure 9C:
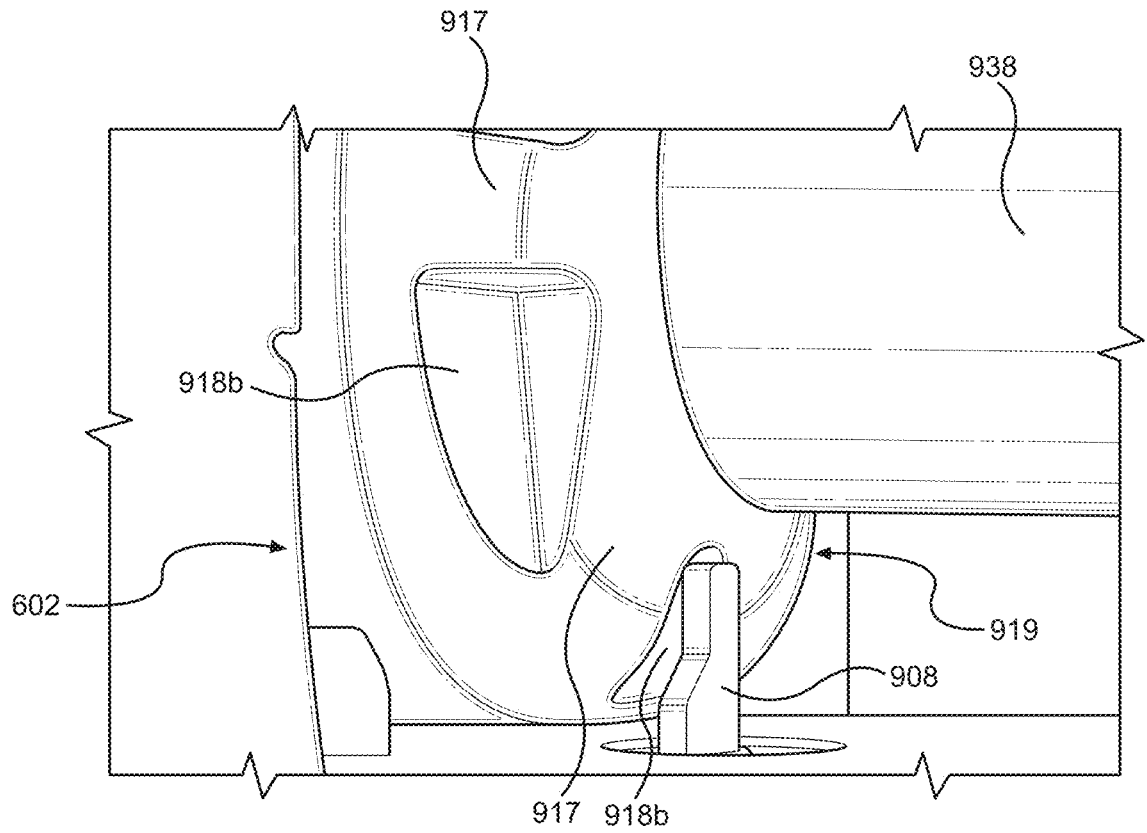

FIGS. 9A-9C illustrate a cartridge stabilization system in accordance with an embodiment of the current invention. In some embodiments, a cartridge 902 is inserted into a cartridge bay. Optionally, a leading face 919 of cartridge 902 approaches an interference element 908. As the cartridge approaches full insertion, face 919 optionally contacts the interference element 908 either in alignment (with a complementary interference element 917 of the cartridge aligned to interference element 908) or not in alignment. For example, when the face 919 contacts the interference element 908 not in alignment (for example as illustrated in FIG. 9B), the cartridge 902 is optionally reoriented 955 until it aligns with the interference element 908. For example, when the cartridge 902 is in alignment, the complementary interference element 917 on the leading face 919 of the cartridge may in interlock with the interference element 908 of the delivery device (for example as illustrated in FIG. 9C). Once the interface elements are interlocked, the orientation of the cartridge 902 is optionally locked with respect to the delivery device. In some embodiments, when the cartridge 902 is locked further action of the driver powers pharmaceutical delivery.

FIG. 9A shows leading face 919 of a cartridge 902 approaching interference element 908 in accordance with an embodiment of the current invention. Optionally, leading face 919 of cartridge 902 includes protruding sections 917 and indentations 918a, 918b and 918c. For example, in FIG. 9A protrusions 917 include complementary interference elements that interlock with interference element 908. In the example of FIG. 9A, leading face 919 is approaching interference element 908 out of alignment. For example, complimentary interference elements 917 are not aligned to interlock with interference element 908 in the illustrated orientation of cartridge 902.

In some embodiments, the interference element 908 includes a pin. For example in the embodiment of FIGS. 9A-9C, the complimentary interference elements include a protrusion 917. Optionally a protruding interference element may be part of the cartridge and/or the delivery device. Optionally an interference element of the delivery device may include an elastic part. Alternatively or additionally, an interference element on the cartridge may include an elastic part. Optionally cartridge 902 includes a connector 938. For example, connector 938 may include a septum. For example, septum may connect to a needle 638 of the delivery device. Alternatively or additionally, a connector on a cartridge may include a needle. For example, the needle may connect to a septum of a delivery device.

In some embodiments, a leading face of a cartridge reaches the interference elements 908 of the delivery device out of alignment. Optionally, the driver realigns the cartridge 902 into alignment with interference element 908. For example, when the cartridge 902 is fully inserted, protrusion 917 overlaps and/or pushes interference element 908 out of the way. For example, interference element 908 is displaced elastically. Pushing interference element 908 optionally adds a resistance to insertion of the cartridge. For example, displacement of interference element 908 may be by elastic flexing of element 908 (for example as illustrated in FIG. 9B). Optionally, elastic displacement of interference element 908 allows cartridge 902 to be fully inserted until it is fixed longitudinally in the cartridge bay.

In some embodiments, after insertion of the cartridge 902 into the cartridge bay, a driver is activated. Optionally, the driver reorients cartridge 902. For example, cartridge 902 is rotated as Illustrated by arrow 955 in FIG. 9B. Optionally rotation of the cartridge continues until interference element 908 is overlaps with indentation 918b. Once the interference element 908 is overlaps indentation 918b, interference element 908 optionally snaps into indentation 918b. For example, by snapping into the indentation 918b, interference element 908 locks the orientation of cartridge 902, for example as illustrated in FIG. 9C. Optionally, both edges of an indentation 918b may be at a sharp incline. For example, both sides of an interference element may be sharply angled, for example to lock in either direction. Alternatively or additionally, one side of an indentation 918b may be steeply angled (for example to prevent rotation in that direction) and/or another side may be at a shallow angle (for example to allow rotation in that direction). For example, rotation in a preferred direction require between 100% to 50% the torque of rotation in an opposite direction and/or between 50% to 20% and/or between 20% to 5% and/or between 5% to 1% and/or less that 1% as much force as rotating in the opposite (prevented) direction.

In some embodiments, when interference element 908 is interlocked with complimentary interference element 917, cartridge 902 is locked and it is orientation with respect to the delivery device, for example, as Illustrated in FIG. 9C. For example, when interference elements 908 overlaps a protrusion 917, cartridge 902 may rotate until an indentation 918b overlaps with interference element 908 and/or interference element 908 is in alignment for locking with complimentary interference 917. For example, when indentation 918b overlaps with interference element 908, interference element 908 optionally snaps into indentation 918b locking the orientation of cartridge 902. Alternatively or additionally, the cartridge 902 may be inserted with interference elements 908 and 917 already in locking alignment. For example, interference element 908 may immediately slip into an indentation 918a-918c. When indentations 918a-918c and 908 overlap and cartridge 902 it is fully inserted, interference element 908 may be unstressed. Alternately or additionally, interference element 908 may be displaced elastically when it is overlaps with an indentation 918a-918c. For example, this may give a tactile sign when the cartridge is fully inserted when the two interference elements 908 and 917 are aligned to interlock.

Exemplary Interfaces Between a Driver and a Reservoir

Figure 10:
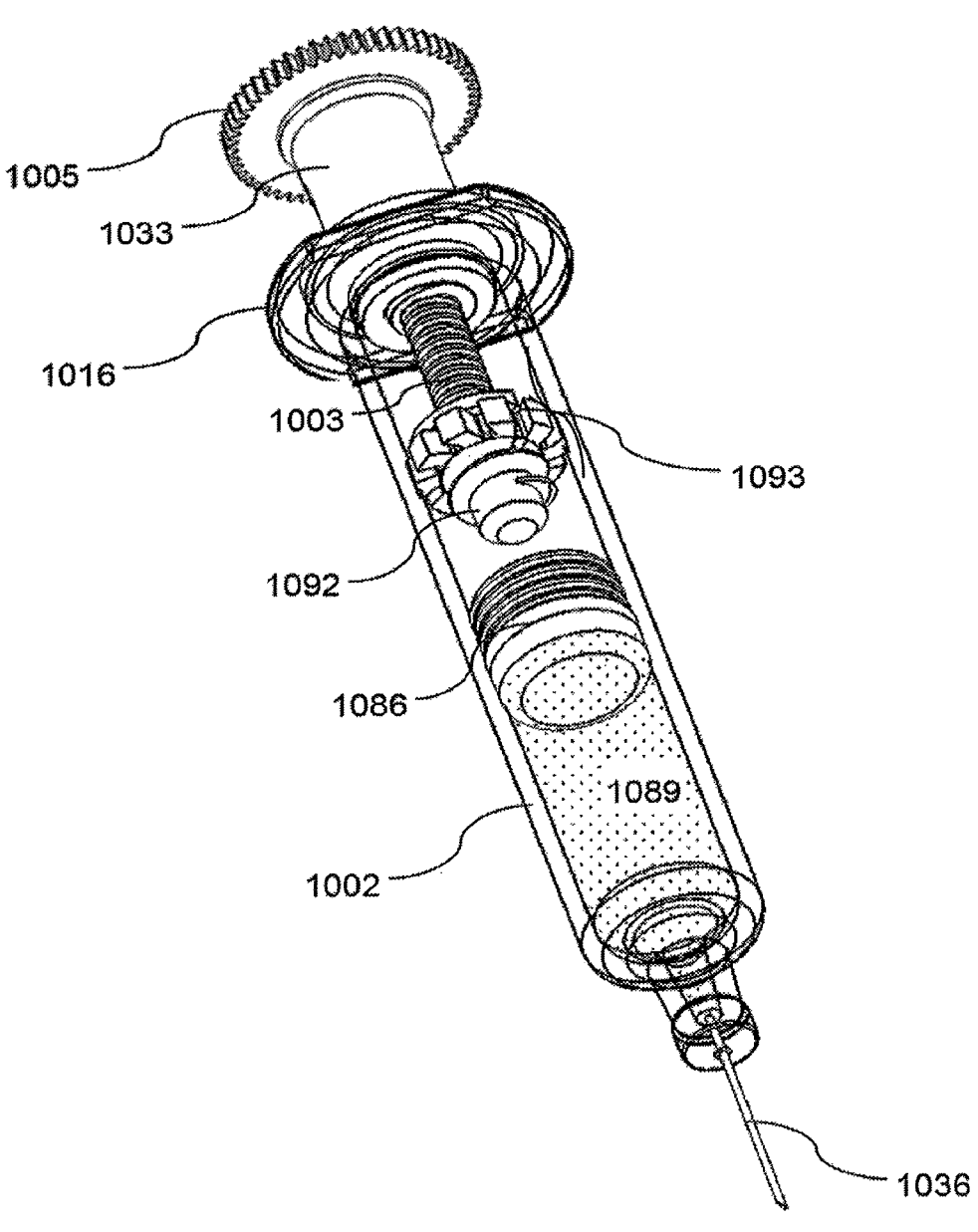
FIG. 10 is a schematic illustration of a pharmaceutical cartridge in accordance with an embodiment of the current invention.

FIG. 10 is a schematic illustration of a pharmaceutical cartridge in accordance with an embodiment of the current invention. In some embodiments, a cartridge may include a driver. Optionally a drive may include one part of the driver that is orientationally stabilized with respect to the reservoir and/or a second part that is translationally stabilized with respect to the reservoir.

In some embodiments, a cartridge includes a driver. For example, a driver may include a TSA. For example, the TSA may include an internally threaded element 1033, which is threadably connected to an externally threaded pushing rod 1003. When element 1033 rotates with respect to rod 1003 the rod is optionally translated with respect to element 1033. Optionally the element is connected to a reservoir 1002 of the cartridge, such that element 1033 does not translate linearly with respect to reservoir 1002 and/or does not separate from reservoir 1002. In some embodiments element 1033 can rotate with respect to reservoir 1002. In some embodiments, rod 1003 is rotationally stabilized with respect to reservoir 1002. Alternatively or additionally, an internally threaded element may be translationally stabilized and/or an externally threaded element may be rotationally stabilized.

In some embodiments, element 1033 is connected to a transmission 1005. For example, transmission 1005 may connect to a motor, which optionally rotates transmission 1005 and/or element 1033 with respect to a delivery device.

In some embodiments rod 1003 is rotationally stabilized with respect to a reservoir 1002. For example, the rod may be connected to a stabilizer pad 1093. Pad 1093 may cause friction between rod 1003 and an inner wall of reservoir 1002. For example when element 1033 is rotated with respect to a reservoir 1002, rod 1003 may rotate with element 1033 and/or alternatively rod 1003 make move linearly with respect to element 1033. Whether rod moves linearly or rotates is optionally controlled by the pitch of the screw threads connecting rod 1003 to element 1033 and/or by the friction between pad 1093 and reservoir 1002.

In some embodiments, rod 1003 is connected to a plunger interface 1092.

Optionally, driving rod 1003 into reservoir 1002 couples plunger interface 1092 to a plunger 1086 in the reservoir 1002. Further driving rod 1003 into reservoir 1002, optionally drives plunger 1086 into reservoir 1002 and/or discharges a pharmaceutical 1089. For example, pharmaceutical 1089 may be discharged out a distal end of reservoir 1002 opposite element 1033. Alternatively or additionally, a cartridge may not include a friction pad 1093. For example, plunger 1086 be connected to rod 1003 and/or plunger 1086 may supply friction between the inner wall of reservoir 1002 and rod 1003.

The cartridge of the exemplary embodiment of FIG. 10 includes a hollow needle 1036. For example when cartridge is inserted into a delivery device, needle 1036 may puncture a septum of the delivery device and/or supply fluid path between reservoir 1002 and the delivery device. A cartridge optionally includes a proximal flange 1016.

In some embodiments, when reservoir 1002 is held stable with respect to a delivery device (for example by means of a cartridge stabilization system) and/or transmission 1005 is rotated with respect to the delivery device, the pharmaceutical is discharged. Alternatively or additionally, when reservoir 1002 is not prevented from rotating with respect to the delivery device, rotating transmission 1005 with respect to the delivery device may rotate reservoir 1002 with respect to the delivery device and/or may not cause discharge of the pharmaceutical 1089.

Figure 11:
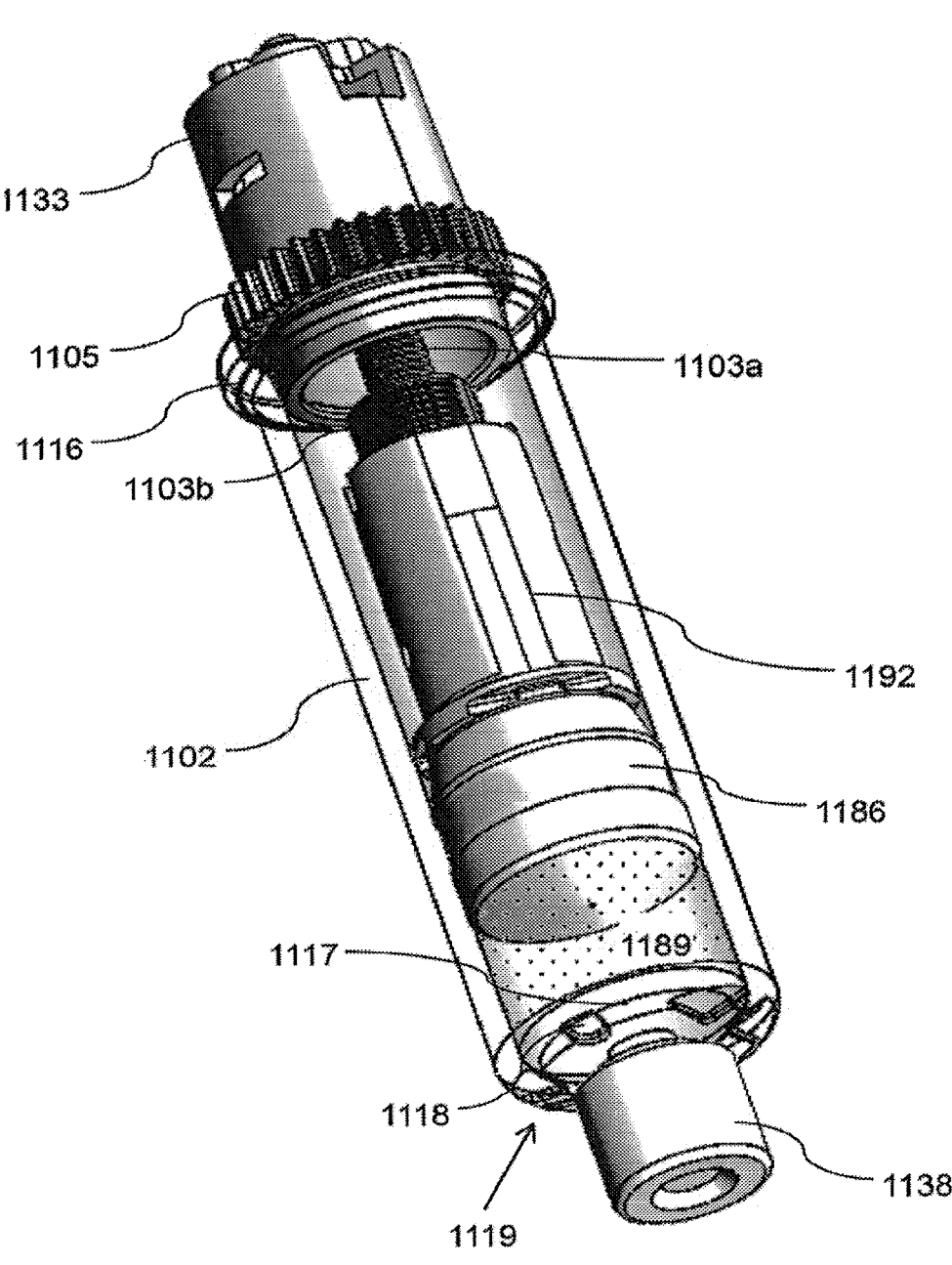
FIG. 11 is a schematic illustration of a pharmaceutical cartridge in accordance with an embodiment of the current invention.

FIG. 11 is a schematic illustration of a pharmaceutical cartridge in accordance with an embodiment of the current invention. In some embodiments, a cartridge may include a driver. Optionally a drive may include one part of the driver that is orientationally stabilized with respect to the reservoir and/or a second part that is translationally stabilized with respect to the reservoir.

In some embodiments, a cartridge includes a driver. For example, a driver may include a TSA. For example, the TSA may include a containing element 1133, which is irrotationally connected to an externally threaded pushing rod 1103a. When element 1133 rotates, rod 1103a is optionally also rotated. Optionally element 1133 is connected to a reservoir 1102 of the cartridge, such that element 1133 does not translate linearly with respect to reservoir 1102 and/or does not separate from reservoir 1102. For example, a shoulder of element 1133 may rest on a flange 1116 of reservoir 1102. In some embodiments element 1133 can rotate with respect to reservoir 1102. In some embodiments, rod 1103a threadably connected to a second rod 1103b. For example, rod 1103b includes an inner thread, which is coupled to the outer thread of rod 1103a. Additionally or alternatively, rod 1103b includes an out thread that is coupled to an inner thread of a plunger interface 1192.

In some embodiments, element 1133 is connected to a transmission 1105. For example, transmission 1105 may connect to a motor, which optionally rotates transmission 1105 and/or element 1133 with respect to a delivery device.

In some embodiments, plunger interface 1192 is connected to a plunger 1186. Plunger 1186 is optionally in friction contact with an inner wall of reservoir 1102. For example when element 1133 is rotated with respect to a reservoir 1102, rod 1103a may rotate with rod 1103b and/or alternatively rod 1103a rotate with respect to and/or move linearly with respect to rod 1103b. Alternatively or additionally, when rod 1103b is rotated with respect to a reservoir 1102, rod 1103b may rotate with plunger interface 1192 and/or alternatively rod 1103b rotate with respect to and/or move linearly with respect to plunger interface 1192. Whether parts moves linearly or rotate is optionally controlled by the pitch of the screw threads and/or by the friction between plunger 1186 and reservoir 1102.

Optionally, driving interface 1192 into reservoir 1102, optionally drives plunger 1186 into reservoir 1102 and/or discharges a pharmaceutical 1189. For example, pharmaceutical 1189 may be discharged out a distal end of reservoir 1102 opposite element 1133. For example, plunger 1186 be connected to interface 1192 and/or plunger 1186 may supply friction between the inner wall of reservoir 1102 and interface 1192 for example inhibiting rotation of interface 1192 with respect to reservoir 1102.

The cartridge of the exemplary embodiment of FIG. 11 includes a septum 1138. For example when cartridge is inserted into a delivery device, a needle of the delivery device may puncture a septum of the delivery device and/or supply fluid path between reservoir 1102 and the delivery device.

In some embodiments, when reservoir 1102 is held stable with respect to a delivery device (for example by means of a cartridge stabilization system) and/or transmission 1105 is rotated with respect to the delivery device, the pharmaceutical is discharged. Alternatively or additionally, when reservoir 1102 is not prevented from rotating with respect to the delivery device, rotating transmission 1105 with respect to the delivery device may rotate reservoir 1102 with respect to the delivery device and/or may not cause discharge of the pharmaceutical 1189.

FIG. 11 shows leading face 1119 of reservoir 1102 in accordance with an embodiment of the current invention. Optionally, leading face 1119 of reservoir 1102 includes protruding sections 1117 and/or indentations 1118. For example, a protrusion 1117 may include a complementary interference element that interlocks with an interference element of the delivery device.

Exemplary Dimensions of a Drug Delivery Device

In some embodiments the payload of a reservoir (for example a syringe) may include, for example between 0.5 and 2 ml and/or between 2 and 5 ml and/or between 5 and 7 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor as discussed, including for example a DC motor, an actuator, a brushless motor, and/or a transmission including for example a tele-scoping assembly and/or a threaded interference element and/or a gear and/or a coupling and/or an elastic mechanism (for example a spring and/or a rubber band) and/or an expanding gas and/or a hydraulic actuator).

A drug delivery device in accordance with some embodi-ments of the present invention may include a reservoir part as discussed. For example, a reservoir may include a medi-cine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of the barrel. The sterility of all and/or part of the needle may for example be protected by a protective cap. The protective cap may remain on the needle when the syringe is supplied and/or installed into an injector. For example, the medicine container may option-ally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example, the force required to inject the drug may depend on the injection rate and/or the viscosity of the drug and/or the syringe geometry and/or the needle dimensions.

In some embodiments, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguard-ing is triggered) may range for example between to 0.5 to 2 and/or from 2 to 7 and/or from 7 to 10 N*cm.

During injection, the linear movement of a plunger may range for example between 10-50 mm. The length of move-ment of the plunger may vary for example with the volume of medicine to be injected that may range for example between 0.5 to 3 ml.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 70 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate.

For example an expected time of discharge may range for example between 24 to 78 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 70 cp) and/or between 120 seconds and 3 minutes for larger volumes and/or viscosities. In some embodiments, injection times may be longer. The length of the injection time may be determined by consid-erations other than viscosity and/or volume.

In some embodiments, the reservoir may have a length ranging for example between 20 and 72 and/or 72 and 78 mm and/or 78 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments, an extension may have a straight end portion with a length ranging for example between 1 and 3 mm or 3 and 7 mm or 7 and 8 or 8 and 10 mm or 10 and 15 mm or 15 and 50 mm. In some embodi-ments, the exposed straight portion of a needle may have a length ranging for example between 1 and 5 mm or 5 and 7 mm or 7 and 10 mm or 10 and 20 mm.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%.

The terms "comprises", "comprising", "includes", "including", "having" and their conjugates mean "including but not limited to".

The term "consisting of" means "including and limited to".

The term "consisting essentially of" means that the com-position, method or structure may include additional ingre-dients, steps and/or parts, but only if the additional ingre-dients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accord-ingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those interference elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of loading a cartridge having a cylindrical reservoir into a delivery device, the method comprising:
   inserting the cartridge into a cartridge bay of the delivery device in a first rotational orientation about a longitudinal axis of the cartridge thereby longitudinally displacing a first interference element of the delivery device;
   powering a motor of the delivery device to apply a torque to the cartridge to rotate the cartridge to a second rotational orientation about the longitudinal axis of the cartridge; and
   interlocking a second interference element of the cartridge with the first interference element on the delivery device to lock the cartridge in the second rotational orientation.

2. The method of claim 1, wherein the first interference element of the delivery device is elastically displaced as a result of the inserting of the cartridge, and wherein the first interference element is at least partially released when the cartridge reaches the second rotational orientation.

3. The method of claim 2, wherein elastic displacement of the first interference element produces a resistance to the inserting of the cartridge, the method further comprising:
   fixing the cartridge in the cartridge bay after the first interference element is elastically displaced to at least partially counteract the resistance produced by the elastic displacement of the first interference element.

4. The method of claim 1, wherein interlocking the second interference element with the first interference element inhibits rotation of the cartridge around the longitudinal axis.

5. The method of claim 1, wherein the first interference element contacts the cartridge once the cartridge is more than 97% inserted into the cartridge bay.

6. The method of claim 1, wherein the cartridge is a syringe, a vial, or an ampoule.

7. The method of claim 1, wherein the cylindrical reservoir contains a pharmaceutical.

8. The method of claim 1, wherein the motor is powered by a chemical potential or mechanical potential.

9. The method of claim 1, wherein the motor is powered by a battery.

10. A method of discharging a pharmaceutical from a cartridge using a delivery device, the method comprising:
    inserting the cartridge longitudinally into a cartridge bay of the delivery device in a first rotational orientation about a longitudinal axis of the cartridge thereby longitudinally displacing a first interference element of the delivery device;
    applying a torque to the cartridge with a driver of the delivery device to rotate the cartridge to a second rotational orientation about the longitudinal axis of the cartridge;
    interlocking a second interference element of the cartridge with the first interference element on the delivery device to lock the cartridge in the second rotational orientation; and
    continuing to apply torque to the cartridge with the driver of the delivery device to discharge the pharmaceutical from the cartridge.

11. The method of claim 10, wherein the torque applied to the cartridge to rotate the cartridge to the second rotational orientation is less than the torque applied to the cartridge to discharge the pharmaceutical from the cartridge.

12. The method of claim 10, wherein the driver applies the torque to a threaded element that is threadably connected to a second threaded element, and wherein the second threaded element is inhibited from rotating around the longitudinal axis with respect to the cartridge.

13. The method of claim 10, wherein the first interference element of the delivery device is elastically displaced as a result of the inserting of the cartridge, and wherein the first interference element is at least partially released when the cartridge reaches the second rotational orientation.

14. The method of claim 13, wherein elastic displacement of the first interference element produces a resistance to the inserting of the cartridge, the method further comprising:
    fixing the cartridge in the cartridge bay after the first interference element is elastically displaced to at least partially counteract the resistance produced by the elastic displacement of the first interference element.

15. The method of claim 10, wherein interlocking the second interference element with the first interference element inhibits rotation of the cartridge around the longitudinal axis.

16. The method of claim 10, wherein the first interference element contacts the cartridge once the cartridge is more than 97% inserted into the cartridge bay.

17. The method of claim 10, wherein the cartridge is a syringe, a vial, or an ampoule.

* * * * *